(12) United States Patent
Aylward et al.

(10) Patent No.: US 8,233,681 B2
(45) Date of Patent: Jul. 31, 2012

(54) METHODS, SYSTEMS, AND COMPUTER PROGRAM PRODUCTS FOR HIERARCHICAL REGISTRATION BETWEEN A BLOOD VESSEL AND TISSUE SURFACE MODEL FOR A SUBJECT AND A BLOOD VESSEL AND TISSUE SURFACE IMAGE FOR THE SUBJECT

(75) Inventors: Stephen Aylward, Carrboro, NC (US); Elizabeth Bullitt, Durham, NC (US); Julien Jomier, Chapel Hill, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 1257 days.

(21) Appl. No.: 11/663,661

(22) PCT Filed: Sep. 26, 2005

(86) PCT No.: PCT/US2005/034289
§ 371 (c)(1),
(2), (4) Date: Dec. 20, 2007

(87) PCT Pub. No.: WO2006/036842
PCT Pub. Date: Apr. 6, 2006

(65) Prior Publication Data
US 2008/0247622 A1    Oct. 9, 2008

Related U.S. Application Data

(60) Provisional application No. 60/613,166, filed on Sep. 24, 2004.

(51) Int. Cl.
*G06K 9/00* (2006.01)

(52) U.S. Cl. ........................ 382/128; 600/424

(58) Field of Classification Search .......... 382/128–132; 600/424–427
See application file for complete search history.

(56) References Cited

U.S. PATENT DOCUMENTS

| 5,438,989 A | 8/1995 | Hochman et al. |
| 5,768,405 A | 6/1998 | Makram-Ebeid |
| (Continued) | | |

FOREIGN PATENT DOCUMENTS

WO    WO 2005/023086 A2    3/2005

OTHER PUBLICATIONS

Notice of Allowance and Fee(s) Due for U.S. Appl. No. 10/569,436 (Sep. 14, 2011).

(Continued)

*Primary Examiner* — Aaron W Carter
(74) *Attorney, Agent, or Firm* — Jenkins, Wilson, Taylor & Hunt, P.A.

(57) ABSTRACT

Methods, systems, and computer program products for hierarchical registration (102) between a blood vessel and tissue surface model (100) for a subject and a blood vessel and tissue surface image for the subject are disclosed. According to one method, hierarchical registration of a vascular model to a vascular image is provided. According to the method, a vascular model is mapped to a target image using a global rigid transformation to produce a global-rigid-transformed model. Piecewise rigid transformations are applied in a hierarchical manner to each vessel tree in the global-rigid-transformed model to perform a piecewise-rigid-transformed model. Piecewise deformable transformations are applied to branches in the vascular tree in the piecewise-transformed-model to produce a piecewise-deformable-transformed model.

21 Claims, 17 Drawing Sheets

U.S. PATENT DOCUMENTS

| | | | |
|---|---|---|---|
| 5,787,185 A | 7/1998 | Clayden | |
| 5,835,189 A | 11/1998 | Quigley et al. | |
| 6,148,095 A * | 11/2000 | Prause et al. | 382/131 |
| 6,169,917 B1 | 1/2001 | Masotti et al. | |
| 6,173,068 B1 | 1/2001 | Prokoski | |
| 6,443,894 B1 | 9/2002 | Sumanaweera et al. | |
| 6,563,941 B1 | 5/2003 | O'Donnell et al. | |
| 6,581,011 B1 | 6/2003 | Johnson et al. | |
| 6,690,816 B2 | 2/2004 | Aylward et al. | |
| 6,711,433 B1 | 3/2004 | Geiger et al. | |
| 8,090,164 B2 * | 1/2012 | Bullitt et al. | 382/128 |
| 2001/0036302 A1 | 11/2001 | Miller | |
| 2002/0086347 A1 | 7/2002 | Johnson et al. | |
| 2002/0106116 A1 | 8/2002 | Knoplioch et al. | |
| 2002/0118875 A1 | 8/2002 | Wilensky | |
| 2002/1013644 | 9/2002 | Vim et al. | |
| 2003/0123606 A1 * | 7/2003 | Mollus et al. | 378/42 |
| 2003/0208116 A1 | 11/2003 | Liang et al. | |
| 2004/0210124 A1 | 10/2004 | Nowinski et al. | |
| 2006/0036167 A1 * | 2/2006 | Shina | 600/433 |
| 2007/0014453 A1 * | 1/2007 | Nowinski et al. | 382/128 |
| 2007/0019846 A1 | 1/2007 | Bullitt et al. | |
| 2007/0123771 A1 * | 5/2007 | Redel et al. | 600/407 |
| 2008/0262341 A1 * | 10/2008 | Boyden et al. | 600/424 |
| 2009/0080746 A1 * | 3/2009 | Xu et al. | 382/131 |
| 2010/0049034 A1 * | 2/2010 | Eck et al. | 600/424 |
| 2011/0130651 A1 * | 6/2011 | Chen et al. | 600/425 |

OTHER PUBLICATIONS

Notice of Allowance and Fee(s) Due for U.S. Appl. No. 10/569,436 (Jun. 9, 2011).
Final Official Action for U.S. Appl. No. 10/569,436 (Nov. 23, 2010).
Non-Final Official Action for U.S. Appl. No. 10/569,436 (May 11, 2010).
Restriction Requirement for U.S. Appl. No. 10/569,436 (Mar. 12, 2010).
Alazzaz et al., Intracranial percutaneous transluminal angioplasty for arteriosclerotic stenosis, Arch. Neurol., vol. 57, pp. 1625-1630 (2000).
Alperin et al., "Retrospective Registration of X-ray Angiograms with MR Images by Using Vessels as Intrinsic Landmarks," Journal of Magnetic Resonance Imaging, 4: pp. 139-144 (1994).
Amunts et al., "Advances in Cytoarchitectonic Mapping of the Human Cerebral Cortex," Neuroimaging Clinics of North America, vol. 11, No. 2, pp. 151-169 (May 2001).
Aylward et al., "Analysis of the parameter space of a metric for registering 3D vascular images," MICCAI 2001; Lecture Notes in Computer Science, vol. 2208, pp. 932-939 (2001).
Aylward et al., "Initialization, Noise, Singularities, and Scale in Height Ridge Traversal for Tubular Object Centerline Extraction," IEEE Transactions on Medical Imaging, vol. 21, No. 2, pp. 61-75 (2002).
Aylward et al., "Intensity Ridge and Widths for Tubular Object Segmentation and Description," IEEE Workshop on Mathematical Methods in Biomedical Image Analysis, pp. 131-138 (1996).
Aylward et al., "Registration and Analysis of Vascular Images," International Journal of Computer Vision, vol. 55, No. 3, pp. 123-138 (Nov. 2003).
Ballard, "Generalizing the Hough transform to detect arbitrary shapes," Pattern Recognition, vol. 13, No. 2, pp. 111-122 (1981).
Bénard et al., "Imaging Gliomas with Positron Emission Tomography Tomography," Seminars in Nuclear Medicine, vol. 33, pp. 148-162 (Apr. 2003).
Besl et al., "A method for registration of 3-D shapes" IEEE Trans. Pattern Anal. Mach. Intell. 14, 1992, pp. 239-256 (1992).
Bracher, "Changes in Peripapillary Tortuosity of the Central Retinal Arteries in Newborns," Graefe's Arch Clin Exp Opthalmol, vol. 218, pp. 211-217 (1982).
Brubaker et al., "The Use of Diffusion Tensor Imaging to Evaluate Demyelination Processes in Mice," Abstract, RSNA (2003).
Bullitt et al., "Analyzing attributes of vessel populations," Submitted MedIA, (2003b).
Bullitt et al., "Measuring tortuosity of the intracerebral vasculature from MRA images," IEEE TMI (2003a).
Bullitt et al., "Vascular Attributes and Malignant Brain Tumors," Accepted MICCAI 2003 (2003).
Bullitt, "Volume Rendering of Segmented Image Objects," IEEE-TMI, vol. 21, pp. 998-1002 (2002).
Bullitt et al., "Symbolic Description of Intracerebral Vessels Segmented from Magnetic Resonance Angiograms and Evaluation by Comparison with X-Ray Angiograms," Medical Image Analysis, vol. 5, pp. 157-169 (2001).
Bullitt et al., "Computer-assisted visualization of arteriovenous malformations on the home pc." Neurosurgery: 48: 2001, pp. 576-583 (2001).
Bullitt et al., "Registration of 3D Cerebral Vessels with 2D Digital Angiograms: Clinical Evaluation," Academic Radiology, vol. 6, No. 9, pp. 539-546 (Sep. 1999).
Bullitt et al., "3D Graph Description of the Intracerebral Vasculature from Segmented MRA and Tests of Accuracy by Comparison with X-ray Angiograms," IPMI'99, Lecture Notes in Computer Science, vol. 1613, pp. 308-321 (1999).
Bullitt et al., "Methods for displaying intracerebral vascular anatomy," American Journal Neuroradiology, vol. 18, pp. 417-420 (1997a).
Bullitt et al., "Three dimensional reconstruction of curves from pairs of projection views in the presence of error. I. Algorithms," Am. Assoc. Phys. Med., vol. 24, No. 11 pp. 1671-1678 (Nov. 1997).
Bullitt et al., "Three dimensional reconstruction of curves from pairs of projection views in the presence of error. II. Analysis of error," Am. Assoc. Phys. Med., vol. 24, No. 11, pp. 1679-1687 (Nov. 1997).
Bullitt et al., "Three-dimensional reconstruction of intracranial vessels from biplane projection views," Journal of Neurosciience Methods, vol. 66, pp. 13-22 (1996).
Capowski et al., "A Numeric Index Based on Spatial Frequency for the Tortuosity of Retinal Vessels and its Application to Plus Disease in Retinopathy of Prematurity," Retina, vol. 15, pp. 490-500 (1995).
Chillet et al., "Vascular atlas formation using a vessel-to-image affine registration method," MICCAI 2003 (2003).
Christoforidis et al., "Visualization of Microvascularity in Glioblastoma Multiforme with 8T High-Spatial Resolution MR Imaging," AJNR, vol. 23, pp. 1553-1556 (Oct. 2000).
Chui et al., "A Unified Feature Registration Method for Brain Mapping." Information Processing in Medical Imaging, pp. 300-314 (2001).
Chung et al., "Statistical 3D Vessel Segmentation using a Rician Distribution," MICCAI '99, Lecture Notes in Computer Science, vol. 1679, pp. 82-89 (1999).
Collignon et al., "Automated multi-modality image registration based on information theory," Information Processing in Medical Imaging 1995 ed Y Bizais, C Barillot and R Di Paola (Dordrecht: Kluwer Academic, pp. 263-274 (1995).
Cool et al., "Tissue-based affine registration of brain images to form a vascular density atlas," MICCAI 2003 (2003).
Cootes et al., "The use of active shape models for locating structures in medical images," Information Processing in Medical Imaging, Lecture Notes in Computer Science, vol. 687, pp. 33-47 (1993).
Cramer et al., "Mapping Individual Brains to Guide Restorative Therapy after Stroke: Rationale and Pilot Studies," Neurological Research, vol. 25, pp. 811-814 (Dec. 2003).
Damon, "Determining the Geometry of the Boundaries of Objects from Medial Data," International Journal of Computer Vision, vol. 63, No. 1, pp. 45-64 (2005).
Danielsson, "Euclidean Distance Mapping," Computer Graphics and Image Processing, (vol. 14, pp. 227-248 (1980).
De Bruijne et al., "Active Shape Model Based Segmentation of Abdominal Aortic Aneurysms in CTA Images," Proceedings of SPIE, vol. 4684, pp. 463-474 (2002).
Du et al., "Vessel Enhancement Filtering in Three-dimensional MR Angiography," Journal of Magnetic Resonance Imaging, 5: 353-359 (1995).
Feldmar et al., "Matching 3D MR Angiography Data and 2D X-ray Angiograms," Lect Notes Comp Sci, vol. 1205, pp. 129-138 (1997).
Frangi et al., "Quantification of Vessel Morphology from 3D MRA," MICCAI '99, LNCS 1679, pp. 358-368 (1999).

Gerig et al., "Symbolic description of 3-D structures applied to cerebral vessel tree obtained from MR angiography volume data," IPMI 1993, Lect. Notes Comp. Sci., Berlin, Germany: Springer, vol. 687, pp. 94-111 (1993).

Goldbaum et al., "Automated Measures of Retinal Blood Vessel Tortuosity," Investigative Ophthalmology & Visual Science, vol. 35, No. 4, p. 2089 (Mar. 15, 1994).

Guyon et al., "VETOT, Volume Estimation and Tracking Over Time: Framework and Validation," MICCAI 2003, LNCS 2879, pp. 142-149 (Mar. 2003).

Hart et al., "Measurement in Classification of Retinal Vascular Tortuosity," International Journal of Medical Informatics, vol. 53, pp. 239-252 (1999).

Ho et al., "Level set evolution with region competition: Automatic 3D segmentation of brain tumors," Proc. 16th Int Conf on Pattern Recognition, IEEE Computer Society, pp. 532-535 (2002).

Holland, "Animal models of cell cycle dysregulation and the pathogenesis of gliomas," Journal of Neuro-Oncology, vol. 51, pp. 265-276 (2001).

Holland, "Brain tumor animal models: importance and progress," Curr Opin Oncol., vol. 13, pp. 143-147 (2001).

Hoogeveen et al., "Limits to the Accuracy of Vessel Diameter Measurement in MR Angiography," Journal of Magnetic Resonance Imaging, 8: 1228-1235 (1998).

Ibanez et al., "Registration Patterns: The Generic Framework for Image Registration of the Insight Toolkit," IEEE International Symposium on Biomedical Imaging, pp. 345-348 (2002).

Jain, "Normalizing Tumor Vasculature with Anti-Angiogenic Therapy: A New Paradigm for Combination Therapy," Nature Medicine, vol. 7, pp. 987-989 (Sep. 2001).

Kahn et al., "Diagnosis of Recurrent Brain Tumor: Value of 201T1 SPECT vs 18F-fluorodeoxyglucose PET," AJR, vol. 163, pp. 1459-1465 (1994).

Kaufman et al., "Diagnostic Brain Biopsy," Wilkins RH, Rengachery SS (eds.) Neurosurgery, McGraw-Hill, New York, pp. 289-294 (1985).

Kitamoto et al., "Vascular Endothelial Growth Factor is an Essential Molecule for Mouse Kidney Development: Glomerulogenesis and Nephrogenesis," Journal of Clinical Investigation, vol. 99, pp. 2351-2357 (1997).

Koenderink, "Solid Shape: Chapter 5," Cambridge Mass: MIT Press, pp. 167-194 (1993).

Koller et al., "Multiscale detection of curvilinear structures in 2-d and 3-d image data," Proceedings of the 5th International Conference on Computer Vision, Boston, MA, pp. 864-869 (1995).

Krissian et al., "Model-based detection of tubular structures in 3D images". CVIU, vol. 80, pp. 130-171 (2000).

Kuppusamy et al, "In Vivo Regional Cerebral Blood Volume: Quantitative Assessment with 3D T1-weighted Pre and Postcontrast MR Imaging," Radiology, vol. 201, pp. 106-112 (1996).

Lammert et al., "Induction of Pancreatic Differentiation by Signals from Blood Vessles," Science, vol. 294, pp. 564-567 (Oct. 19, 2001).

Lei et al., "Artery-vein separation via MRA—An image processing approach," IEEE-TMI, vol. 20, pp. 689-703 (2001).

Lorenz et al., "Multi-scale Line Segmentation with Automatic Estimation of Width, Contrast and Tangential Direction in 2D and 3D Medical Images," CVRMed-MRCAS '97, LNCS. vol. 1205, pp. 233-242 (1997).

Lorenzen et al., "High-Dimensional Multi-modal Image Registration," WBIR: 234-243 (2003).

Lorigo et al., "Co-dimension 2 geodesic active contours for MRA segmentation," IPMI 99 Lecture Notes in Computer Science, vol. 1613, pp. 126-139 (1999).

Maes et al., "Multimodality image registration by maximization of mutual information," IEEE Transactions on Medical Imaging, vol. 16, No. 2, pp. 187-198 (Apr. 1997).

Maintz et al., "A Survey of medical image registration," In U. Spetzger, H.S. Stiehl, J.M. Gilsbach (Eds.), Navigated Brain Surgery, pp. 117-136 (Oct. 10, 1997).

Masutani et al., "Vascular shape segmentation and structure extraction using a shape-based region-growing model," Proceedings of Medical Image Computing and Computer-Assisted Intervention, Lecture Notes in Computer Science 1496, pp. 1242-1249 (1998).

Masutani et al, "Quantitative vascular shape analysis for 3D MR-angiography using mathematical morphology," Computer Vision, Virtual Reality and Robotics in Medicine, pp. 449-454 (1995).

Matsumoto et al., "Liver Organogenesis Promoted by Endothelial Cells Prior to Vascular Function," Science, vol. 294, pp. 559-563 (Oct. 19, 2001).

Mattes et al., "Nonrigid Multimodality Image Registration," Medical Imaging 2001, vol. 4322, Proceedings of SPIE (2001).

Miller et al., "Statistical Methods in Computational Anatomy," Statistical Methods in Medical Research, vol. 6, pp. 267-299 (1997).

Moon et al., "Automatic Brain and Tumor Segmentation," Medical Image Computing and Computer Assisted Intervention (MICCAI), LNCS-2488, pp. 372-379 (2002).

Niessen et al., "Enhanced Artery Visualization in Blood Pool MRA: Results in the Peripheral Vasculature," IPMI 1999, in Lect. Notes Comp. Sci. Berlin, Germany: Springer, vol. 1613, pp. 340-345 (1999).

Notification of Transmittal of the International Search Report and the Written Opinion of the International Searching Authority, or the Declaration for International Application No. PCT/US04/22955 (Feb. 11, 2005).

Park et al., "Segmentation of intrathoracic airway trees: A fuzzy logic approach," IEEE Transactions on Medical Imaging, 17(4): 489-497 (1998).

Pennec et al., "Tracking brain deformations in time-sequences of 3D US images," Pattern Recognition Letters, 24(4-5): 801-813 (Feb. 2003).

Pizer et al., "Zoom-invariant vision of figural shape: The mathematics of cores," In Computer Vision and Image Understanding, 69, pp. 55-71 (1998).

Porter et al., "Three-Dimensional Registration and Fusion of Ultrasound and MRI Using Major Vessels as Fiducial Markers," IEEE Transactions on Medical Imaging, vol. 20, No. 4, pp. 354-359 (Apr. 2001).

Prastawa, "Automatic brain and tumor segmentation" (2003(a)).

Prastawa et al., "Robust Estimation for Brain Tumor Segmentation," MICCAI 2003 Proceedings, pp. 530-537 (2003).

Reuze et al., A 3-d moment based approach for blood vessel detection and quantification in MRA. Technology and Health Care, 1: 181-188 (1993).

Ricci et al., "Differentiating Recurrent Tumor from Radiation Necrosis: Time for Re-evaluation of Positron Emission Tomography?," American Journal of Neuroradiology, vol. 19, pp. 407-413 (Mar. 1998).

Roche et al., "Rigid Registration of 3D Ultrasound with MR Images: a New Approach Combining Intensity and Gradient," IEEE Transactions on Medical Imaging, 20(10): 1038-1049 (Oct. 2001).

Rueckert et al., "Non-rigid Registration Using Free-Form Deformations: Application to Breast MR Images," IEEE Transactions on Medical Imaging, vol. 18, No. 18, pp. 712-721 (Aug. 1999).

Sato et al., "Three-dimensional multi-scale line filter for segmentation and visualization of curvilinear structures in medical images," Medical Image Analysis, vol. 2, pp. 143-168 (1998).

Schmalbrock et al, "TOF and BOLD 3D Gradient Echo Imaging of Cerebral Vasculature at 8T," Proc. Intl. Soc. Mag. Reson. Med. 10, p. 1 (2002).

Schnabel et al., "A Generic Framework for Non-Rigid Registration Based on Non-Uniform Multi-Level Free-Form Deformations," MICCAI 2001; LNCS 2208, pp. 573-581 (2001).

Seydel, "Organs Await Blood Vessels' Go Signal," Science, vol. 293, p. 2365 (Sep. 28, 2001).

Smedby et al., "Two-Dimensional Tortuosity of the Superficial Femoral Artery in Early Atherosclerosis," Journal of Vascular Research, vol. 30, pp. 181-191 (1993).

Swallow et al., "Reliability of Functional Localization using fMRI," NeuroImage, vol. 20, pp. 1561-1577 (2003).

Székely et al., "Structural description and combined 3-D display for superior analysis of cerebral vascularity from MRA," SPIE 2359, pp. 272-381 (1994).

Tek et al., "Volumetric segmentation of medical images by three-dimensional bubbles," Proc Workshop on Physics-Based Modeling, IEEE press, pp. 9-16 (1995).

Thees et al, "Dipole Source Localization and fMRI of Simultaneously Recorded Data applied to Somatosensory Categorization", NeuroImage, vol. 18, pp. 707-719 (2003).

Van den Elsen et al., "Automatic Registration of CT and MR Brain Images Using Correlation of Geometrical Features," IEEE Transactions on Medical Imaging, vol. 14, No. 2, pp. 384-396 (Jun. 1995).

Van Dyke et al., "Cancer modeling in the modern era: progress and challenges," Cell 108, pp. 135-144 (2002).

Van Leemput et al., "Automated Model-Based Tissue Classification of MR Images of the Brain," IEEE Transactions on Medical Imaging, vol. 18, No. 10, pp. 897-908 (Oct. 1999).

Viola et al., "Alignment by Maximization of Mutual Information," International Journal of Computer Vision, vol. 24, No. 2, pp. 137-154 (1997).

Wang, "Functional Data Analysis of Populations of Tree-structured Objects," Internet available at: http://midag.cs.unc.edu/pubs/papers/WangH_report.pdf (2002).

Weeks et al., "Volume Estimations Using Conventional Hand Tracing Techniques vs. Automatic Thresholding Techniques: Can We Be More Accurate and Save Time?," Radiological Society of North America, Abstract (Nov. 2001).

West et al., "Retrospective Intermodality Techniques for Images of the Head: Surface-Based Versus Volume-Based," IEEE Transactions on Medical Imaging, vol. 18, No. 2, pp. 144-150 (Feb. 1999).

Wilson et al., "An Adaptive Segmentation Algorithm for Time-of-Flight MRA Data," IEEE Transaction on Medical Imaging, vol. 18, No. 10, pp. 938-945 (Oct. 1999).

Wilson et al., "Evaluation of 3D Image Registration as Applied to MR-Guided Thermal Treatment of Liver Cancer," JRMI 8: 77-84 (1998).

Wilson et al., "Segmentation of Cerebral Vessels and Aneurysms from MR Angiography Data," Lect Notes Comp Sci 1230, pp. 428-433 (1997).

Wink et al., "Vessel Axis Determination Using Wave Front Propagation Analysis," MICCAI 2001, LNCS 2208, pp. 845-853 (2001).

Xu et al., "Randomized Hough Transform (RHT): Basic Mechanisms, Algorithms, and Computational Complexities," CVGIP: Image Understanding, vol. 57, No. 2, pp. 131-154 (Mar. 1993).

Yim et al., "Gray-scale skeletonization of small vessels in magnetic resonance angiography," IEEE Transactions on Medical Imaging, 19(6): 568-576 (2000).

Yoshii et al., "Cerebral Radiation Necrosis with Accumulation of Thallium 201 on Single-Photon Emission CT," AJNR, vol. 17, pp. 1773-1776 (Oct. 1996).

Zhou et al., "The Detection and Quantification of Retinopathy Using Digital Angiograms," IEEE Transactions on Medial Imaging, vol. 13, No. 4, pp. 619-626 (Dec. 1994).

Notification of Transmittal of the International Search Report and the Written Opinion of the International Searching Authority, or the Declaration for International Application No. PCT/US05/34289 (Mar. 20, 2006).

* cited by examiner

METHODS, SYSTEMS, AND COMPUTER PROGRAM PRODUCTS FOR HIERARCHICAL REGISTRATION BETWEEN A BLOOD VESSEL AND TISSUE SURFACE MODEL FOR A SUBJECT AND A BLOOD VESSEL AND TISSUE SURFACE IMAGE FOR THE SUBJECT

RELATED APPLICATIONS

This application claims the benefit of U.S. Provisional Patent Application Ser. No. 60/613,166, filed Sep. 24, 2004; the disclosure of which is incorporated herein by reference in its entirety.

GOVERNMENT INTEREST

This invention was made with U.S. Government support under Grant No. R01 EB000219 awarded by the National Institutes of Health. The U.S. Government has certain rights in the invention.

TECHNICAL FIELD

The subject matter described herein relates to modeling blood vessel and tissue surface images and registering blood vessel and tissue surface models with blood vessel and tissue surface images for a subject. More particularly, the subject matter described herein relates to methods, systems, and computer program products for hierarchical registration between a blood vessel and tissue surface model for a subject and a blood vessel and tissue surface image for the subject.

BACKGROUND ART

In medical applications, such as ultrasound-guided surgery, it may be desirable to register a pre-operative image onto the ultrasound image generated by an ultrasound probe during the surgery. For example, features of interest, such as tumors and lesions, may not be visible in the intra-operative ultrasound image used for surgical guidance. However, these features may be clearly visible in pre-operative images, such as magnetic resonance (MR) and computerized tomography (CT), images. Because these features of interest are visible in the pre-operative images but not in the intra-operative ultrasound images, it is desirable to transcribe or map these features from the pre-operative images to the intra-operative images.

One conventional method for mapping pre-operative image features into intra-operative images involves an image-to-image mapping of the pre-operative image to the intra-operative image. One problem with performing image-to-image mappings is that the image-to-image mappings are typically slow because of the number of pixels or voxels that must be mapped between the two images. For example, some image-to-image mapping techniques can take between five minutes and two hours to converge. Such slow convergence is unsuitable for applications, such as surgical guidance, that require real time changes in the mappings. For example, during ultrasound-guided percutaneous liver surgery, a pre-operative MR or CT image may initially be manually aligned as an overlay with an ultrasound image. During surgery, the liver may move and/or deform when the patient moves or breathes. As a result, the ultrasound image becomes misaligned with the pre-operative image. Similarly, in brain surgery, the brain may settle due to changes in pressure during surgery caused by opening of the skull or tumor removal. These movements also cause the ultrasound image to become misaligned with the pre-operative image.

Current surgical guidance systems attempt to solve this misalignment problem using a joystick or other method that allows manual alignment between the pre-operative and intra-operative images. However, such alignment is rigid and does not account for target image deformation during surgery. In addition, manual re-alignments must be continuously performed during surgery for a subject.

Accordingly, in light of these difficulties associated with conventional methods for aligning pre-operative and intra-operative image data, there exists a need for improved, methods, systems, and computer program products for registration between blood vessel and tissue surface image data.

SUMMARY

According to one aspect, the subject matter described herein includes a method for hierarchical registration between a blood vessel and tissue surface model for a subject and a blood vessel and tissue surface image for the subject.

The method includes generating a blood vessel and tissue surface model from a source blood vessel and tissue surface image for a subject. A plurality of hierarchical registrations between blood vessel models in the blood vessel and tissue surface model and blood vessels in a target blood vessel image for the subject are performed. At least one registration is performed between a tissue surface model in the blood vessel and tissue surface model and a tissue surface in the target blood vessel and tissue surface image. The results of the registrations are transformations between locations in the blood vessel and tissue surface model and locations in the target image data. Based on the transformations in locations, the location of a feature of interest in the target blood vessel and tissue surface image is determined.

The subject matter described herein for implementing hierarchical registration between a blood vessel and tissue surface model and a blood vessel and tissue surface image may be implemented using a computer program product comprising computer executable instructions embodied in a computer readable medium. Exemplary computer readable media suitable for implementing the subject matter described herein include chip memory devices, disk memory devices, application specific integrated circuits, programmable logic devices, and downloadable electrical signals. In addition, a computer program product that implements the subject matter described herein may be located on a single device or computing platform or may be distributed across multiple devices for computing platforms.

BRIEF DESCRIPTION OF THE DRAWINGS

Preferred embodiments of the subject matter described herein will now be explained with reference to the accompanying drawings of which.

DETAILED DESCRIPTION OF THE INVENTION

I. Overall System Operation

Figure 1:
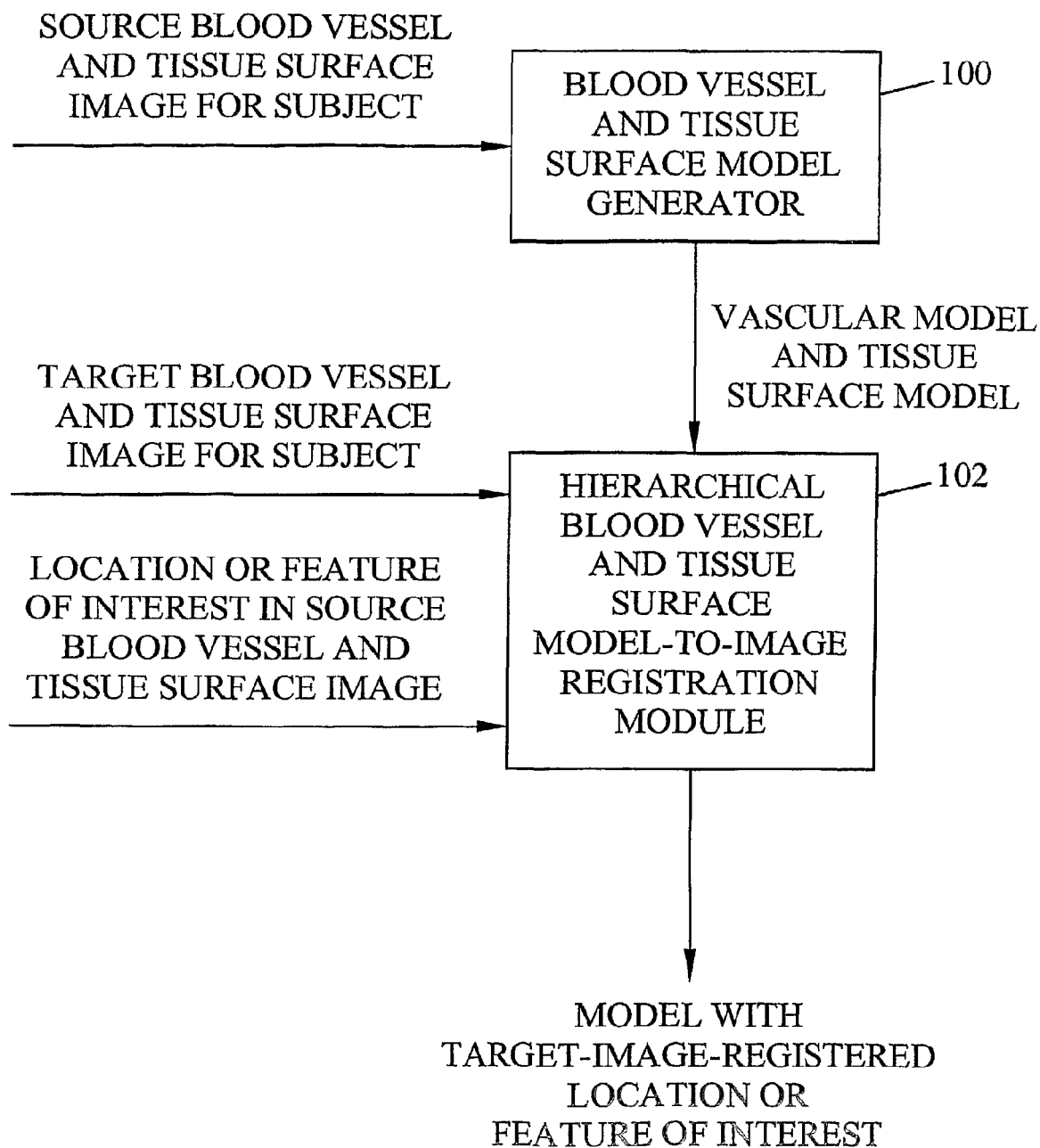
FIG. 1 is a block diagram of exemplary components of a system for hierarchical registration between a blood vessel and tissue surface model and a blood vessel and tissue surface image according to an embodiment of the subject matter described herein.

According to one aspect, the subject matter described herein includes a system for hierarchical registration between a blood vessel and tissue surface model and blood vessel and tissue surface image data. FIG. 1 illustrates such a system. Referring to FIG. 1, a blood vessel and tissue surface model generator 100 receives source blood vessel and tissue surface image for a subject. The source blood vessel and tissue surface image may be an MR image, a CT image, or any other type of image in which blood vessels and tissue surfaces can be distinguished from other features. Blood vessel and tissue surface model generator 100 generates a vascular model and a tissue surface model based on the source blood vessel and tissue surface image. An exemplary method for producing a vascular model and a tissue surface model will be described in detail below.

The system illustrated in FIG. 1 also includes a hierarchical blood vessel and tissue surface model-to-image registration module 102 for registering the models generated by blood vessel and tissue surface module generator 104 with target blood vessel and tissue surface images for the subject using hierarchical piecewise and global registrations. Hierarchical blood vessel and tissue surface model-to-image registration module 102 may receive the models and target blood vessel and tissue surface images for a subject. Hierarchical blood vessel and tissue surface model-to-image registration module 102 may also receive a location or feature of interest in the source blood vessel and tissue surface image to be mapped into the target blood vessel and tissue surface image. For example, the location or feature may be the location of a tumor or an notation made by a physician that corresponds to tumor margins. Hierarchical blood vessel and tissue surface model-to-image registration module 102 may apply a series of hierarchical rigid and deformable registrations to produce a model with a target-image-registered location or feature of interest. For example, in registering a pre-operative MR image of a liver tumor with an intra-operative image of the liver, hierarchical blood vessel and tissue surface model-to-image registration module 102 may utilize the transformations between the locations of the blood vessels and the tissue surfaces to determine the transformation in the location of the tumor from the pre-operative image to the intra-operative image.

The registrations performed by hierarchical blood vessel and tissue surface model-to-image registration module 102 are hierarchical in the sense that blood vessel models in the blood vessel and tissue surface model are mapped to blood vessels in the target image starting from a trunk of each blood vessel and continuing along successive branches of each blood vessel. For example, blood vessels in the human vasculature form tree like structures. The hierarchical blood vessel model-to-image registration method according to the subject matter described herein first registers the trunk of a vessel in the model with a trunk of a vessel in the image. Branches that are children of the trunk are registered along with the trunk. Next, the branches and sub-branches are registered in a hierarchical manner. Piecewise rigid and deformable registrations are both performed in this manner.

Figure 2A:
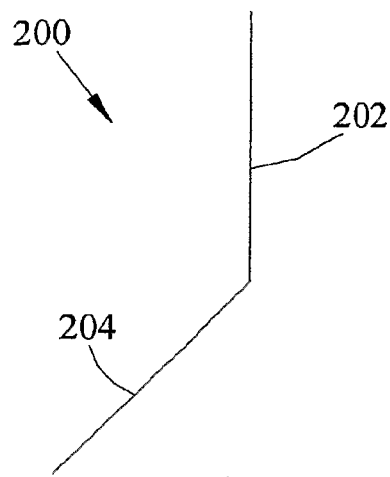
FIGS. 2A-2F are schematic diagrams illustrating hierarchical mapping of a blood vessel model to a blood vessel image according to an embodiment of the subject matter described herein.
Figure 2B:
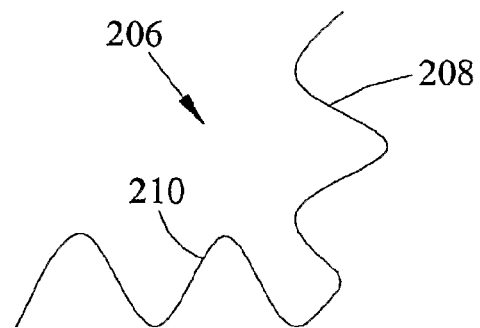
Figure 2C:
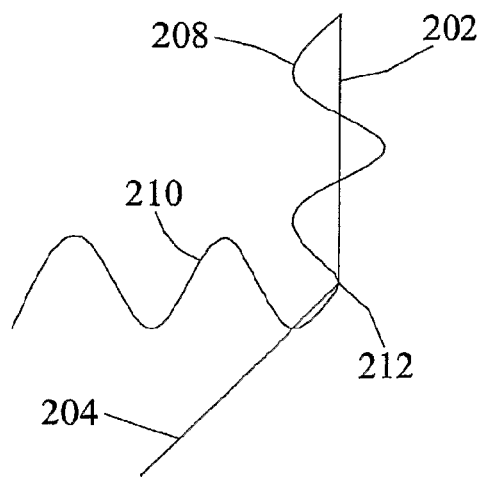
Figure 2D:
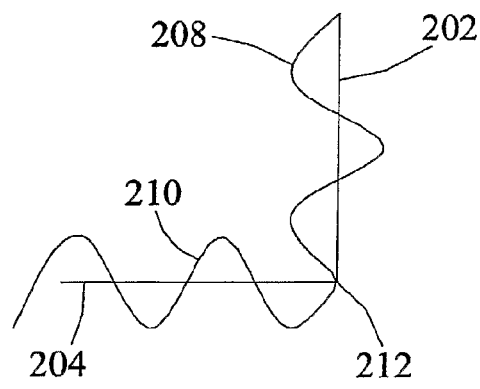

FIGS. 2A-2F illustrate hierarchical registration between a blood vessel model and a blood vessel image according to an embodiment of the subject matter described herein. In FIG. 2A, a blood vessel model 200 includes a root 202 and a single branch 204. Similarly, in FIG. 2B, a blood vessel image 206 includes a root 208 and a single branch 210. In FIG. 2C, root 202 of blood vessel model 200 is translated to the location of root 208 of blood vessel image 206. In FIG. 2D, branch 204 of blood vessel model 200 is rotated about branch point 212 to correspond to the location of branch 210 of blood vessel image 206. The transformations in FIGS. 2A-2D are referred to as rigid transforms because only translations and rotations are performed. That is, a root and branches of in blood vessel model 200 are translated or rotated to correspond to locations of a root and branches blood vessel image 206. The rigid transformations of FIGS. 2A-2D may be repeated for branches and sub-branches in a vessel tree until a model is rigidly registered with an image.

Figure 2E:
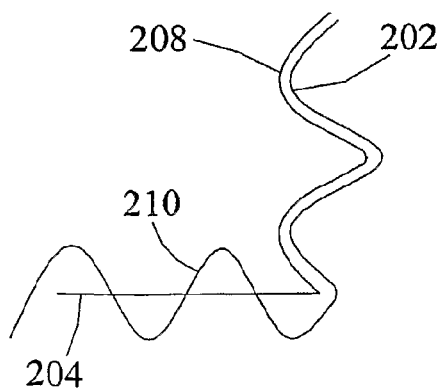
Figure 2F:
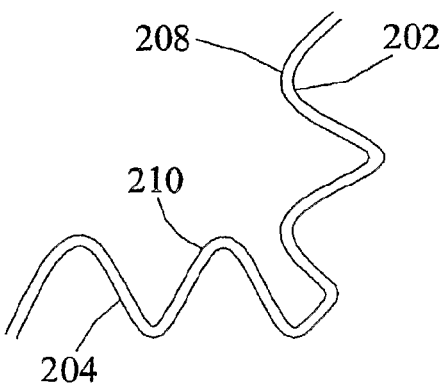

FIGS. 2E and 2F illustrate hierarchical deformable transformations between a blood vessel model and a blood vessel image. In FIG. 2E, root 202 of blood vessel model 200 is deformed to correspond to the shape of root 208 of blood vessel image 206. In FIG. 2F, branch 204 of blood vessel model 200 is deformed to correspond to the shape of branch 210 of blood vessel image 206. Like the rigid transformations, the deformable transformations may be performed in a hierarchical manner on sub-branches until a blood vessel model is deformably registered with a blood vessel image. By performing the registration in a hierarchical manner model-to-image registration time is decreased and registration accuracy is increased.

Figure 3:
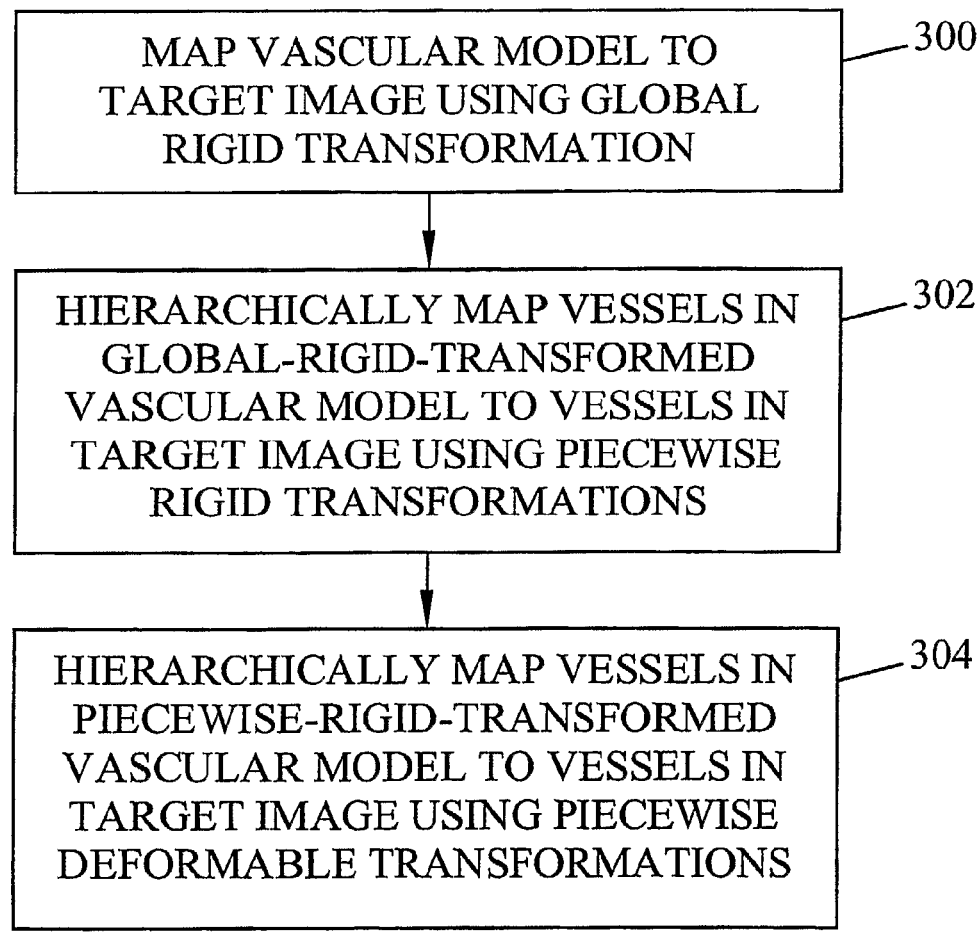
FIG. 3 is a flow chart illustrating an exemplary process for hierarchical mapping between a vascular model and a vascular image according to an embodiment of the subject matter described herein.

According to one aspect, the subject matter described herein includes a method for registering a vascular model with a vascular image for a subject. FIG. 3 is a flow chart illustrating exemplary steps for registering a vascular model with a vascular image according to an embodiment of the subject matter described herein. Referring to FIG. 3, in step 300, a vascular model is mapped to a target image using a global rigid transformation. In step 302, vessels in the global-rigid-transformed vascular model are mapped to vessels in the target image using piecewise rigid transformations. The vessels are mapped in a hierarchical manner from root to branches to sub-branches as illustrated in FIGS. 2A-2F. In step 304, the vessels in the piecewise-rigid-transformed vascular model are mapped to vessels in the target image using piecewise deformable transformations. The deformable transformations are also performed in a hierarchical manner as described above.

Figure 4A:
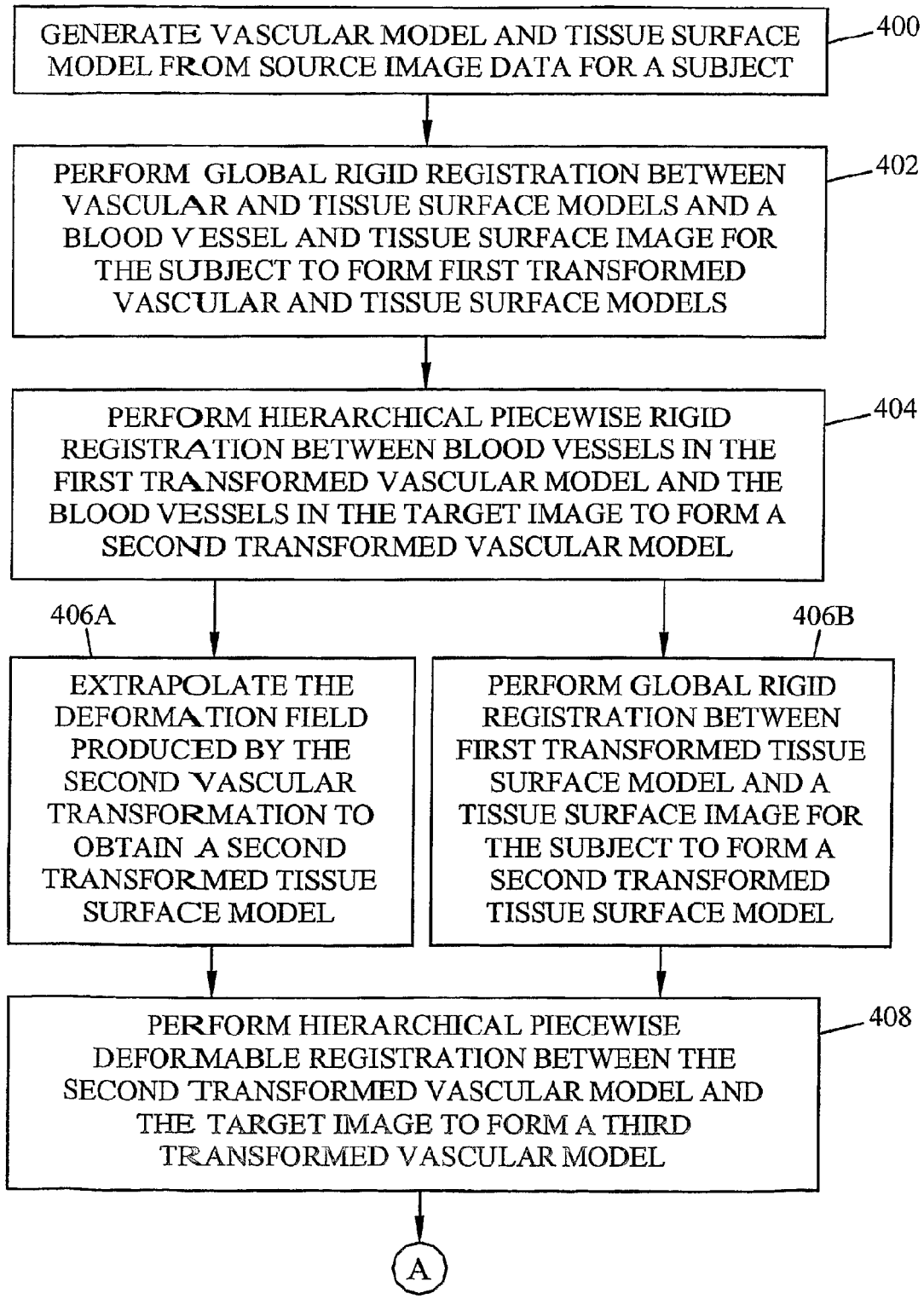
FIG. 4 is a flow chart illustrating an exemplary process for hierarchical mapping between a blood vessel and tissue surface model and a blood vessel and tissue surface image according to an embodiment of the subject matter described herein.
Figure 4B:
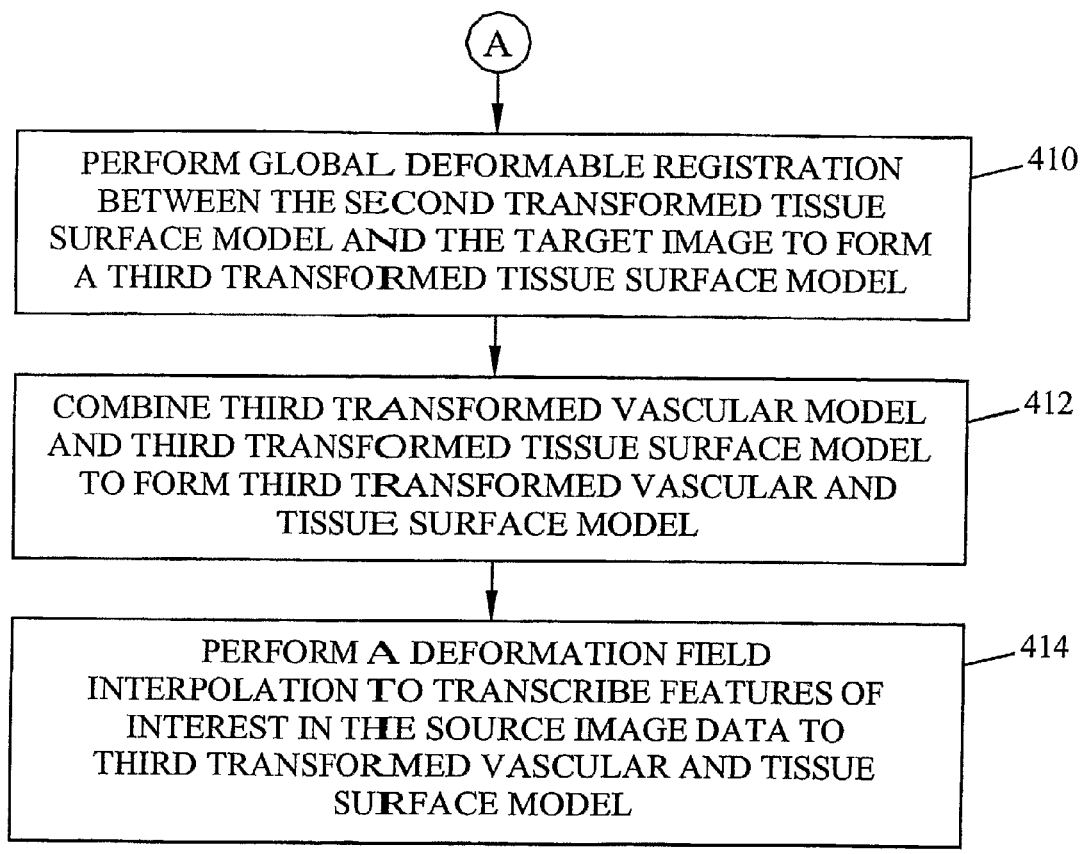

As stated above, in aligning a model with a target image, the blood vessel registration method illustrated in FIG. 3 may be augmented with tissue surface registration. FIG. 4 is a flow chart illustrating exemplary steps for combining tissue surface model-to-image registration with blood vessel model-to-image registration according to an embodiment of the subject matter described herein. Referring to FIG. 4, in step 400, a vascular model and a tissue surface model are generated from image data for a subject. In step 402, a global rigid registration is performed between the vascular and tissue surface models and a blood vessel and tissue surface image for a subject to form a first transformed vascular and tissue surface model. The registration in step 402 may be performed such that the registrations for the vascular and tissue surface models are simultaneously optimized. In step 404, hierarchical piecewise rigid registration is performed between blood vessels in the first transformed vascular model and blood vessels in the target image to form a second transformed vascular model. Step 404 is the same as step 302 illustrated in FIG. 3. Once step 404 is performed, it is necessary to determine how to move the tissue surface model based on movements in the blood vessels in the vascular model. Two options are illustrated in FIG. 4 for registering the tissue surface model after the piecewise rigid blood vessel registration. One option is illustrated in step 406A where the deformation field produced by the second vascular transformation (step 404) is extrapolated to obtain a second transformed tissue surface model. The second alternative is illustrated in FIG. 406B where a global rigid registration is performed between the tissue surface model and the tissue surface image to form the second transformed tissue surface model.

In step 408, a hierarchical piecewise deformable registration is performed between the second transformed vascular model and the target image to form a third transformed vascular model. Step 408 is the same as step 304 illustrated in FIG. 3. In step 410, a global deformable registration is performed between the second transformed tissue surface model and the target image to form a third transformed tissue surface model. In step 412, the third transformed vascular model and the third transformed tissue surface models are combined to form a third transform vascular and tissue surface model.

After step 412, the result is a model in which the vessels and tissue surfaces are transformed from the source image data to the target image data. However, it may be still be desirable to transform other locations or features from the source image data to the target image data. Examples of such locations or features include tumor locations and/or annotations made by a physician in the source image data. Accordingly, in step 414, a deformation field interpolation is performed to transcribe features of interest in the source image data to the third transformed vascular and tissue surface model.

Steps 402-414 may be continually repeated during surgery or other time period in order to continually update registration between the vascular and tissue surface model and the target image as the target image changes. Because the registration is hierarchical and includes both rigid and deformable transformations, the resulting registration is both more accurate and more rapidly converging than conventional image-to-image registration methods. Exemplary methods for performing the steps illustrated in FIG. 4 will now be described in detail.

II. Blood Vessel Model Generation

Blood vessel modeling may be performed using any suitable method that extracts a blood vessel model from blood vessel image data. In one example, a three-dimensional blood vessel modeling or segmentation method according to the subject matter described herein may include performing a multiscale extraction of the centerline of a vessel and then estimating the radius of the vessel about the centerline. Specifically, the method involves three steps:

(1) definition of a seed point on or near a vessel of interest;
(2) automatic, dynamic-scale extraction of an image intensity ridge representing the vessels central skeleton; and
(3) automatic determination of a vessel's radius at each centerline point.

These steps will now be described in detail.

Step 1: A seed point consists of a location $x_0$ and a radius $r_0$ estimate. These values can be specified manually (via points-and-clicks) or automatically using local contrast and ridge measures. An intensity ridge of a tube is defined as a 1D height ridge in 3D:

Define: x as a point in the image ($x \in \Re^3$)
σ as the scale at which measures at x are made $I_\sigma(x)$ as the image intensity at x at scale σ (subscript of an image indicates scaling)

H as the Hessian matrix of I at x at scale σ

$v_i$ and $\lambda_i$ as the eigenvectors and associated eigenvalues of H with $\lambda_1 \leq \lambda_2 \leq \lambda_3$ If x is on a ridge, then $v_3$ approximates the ridge's tangent direction at x, and $v_1$ and $v_2$ approximate the ridge's normal directions.

(See Eberly, "Ridges in Image and Data Analysis," Computational Imaging and Vision, Vol. 7, Kluwer Academic Publishers: Dordrecht (1996).)

Therefore, for x to be a ridge point (i.e., on the centerline of a vessel), it must be true that:

$\lambda_1 \leq \lambda_2 < 0$ Height-Ridge: The intensity decreases away from the ridge $\lambda_2/\lambda_1 \cong 1$ Circularity: Cross-sectional intensity is nearly circular $v_1 \cdot \nabla I_\sigma(x) \cong 0$ Ridgeness: The point is an extremum in the directions normal to the ridge $v_2 \cdot \nabla I_\sigma(x) \cong 0$ Using the eigenvectors of the Hessian to specify the directions in which the point is maximal makes this a "maximum-curvature" height-ridge definition. The scale σ is adapted during the traversal process that is explained next.

Step 2: Given a seed point, the remainder of the extraction process is completely automated; three steps are repeated to traverse the extent of the vessel skeleton. (a) The approximate normal plane is shifted one fifth of a voxel along the ridge's approximate tangent direction. Assuming the ridge varies smoothly, the ridge will pass through this shifted normal plane. (b) The local maximum in intensity in that shifted normal plan is located. This point is the next point $x_{i+1}$ on the ridge/central skeleton. (c) At fixed intervals during this traversal, the radius of the tube $r_i$ is estimated (in a manner similar to that in Step 3—next) and used to define $\sigma_{i+1}$, the scale at which subsequent ridge traversal measures are made. Once any of the height-ridge constraints is not satisfied, the traversal process terminates.

Figure 5:
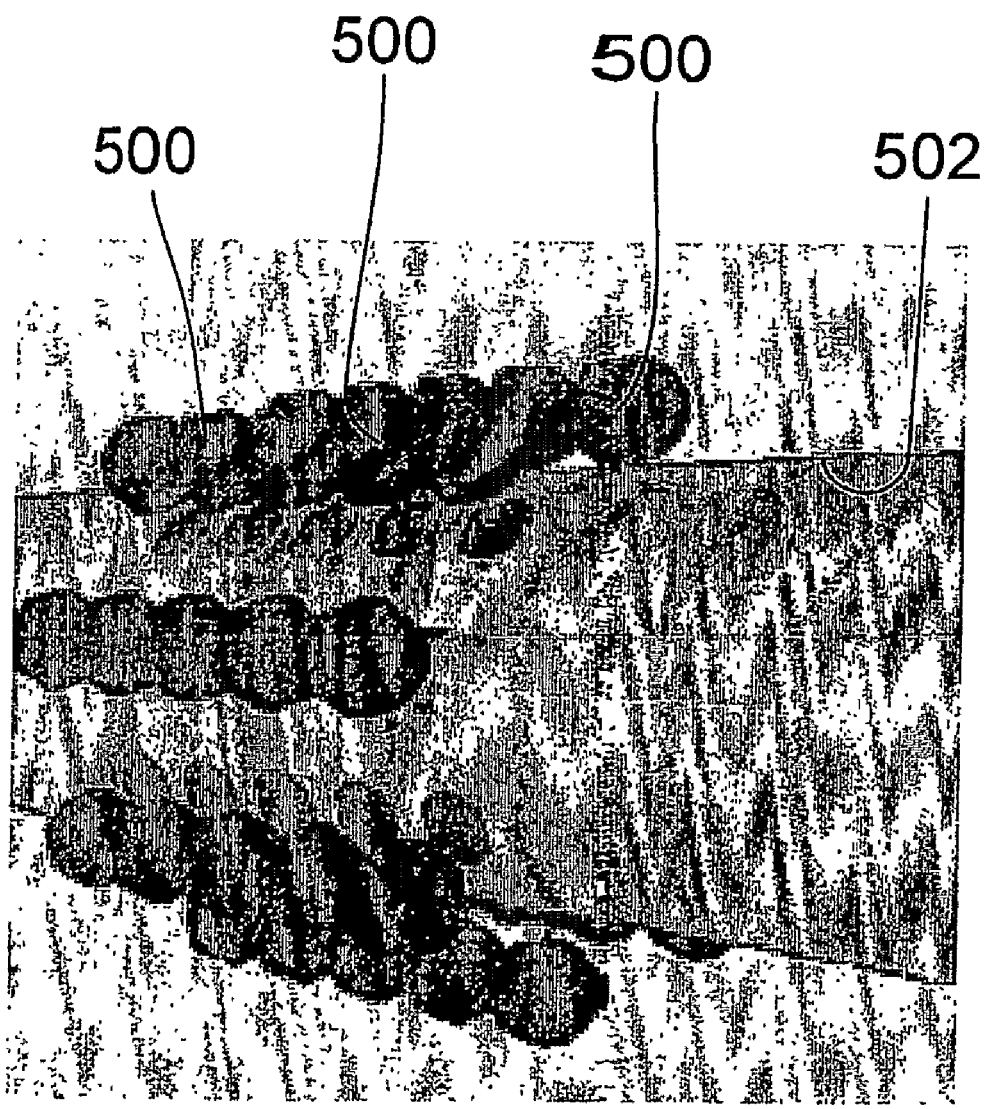
FIG. 5 is a computer-generated image illustrating an exemplary blood vessel model formed using a blood vessel modeling method according to an embodiment of the subject matter described herein.

Step 3: The central track stabilizes the estimation of the tube's radius. The radius at a point $x_i$ on a ridge can be defined by an initial radius estimate $r=r_{i-1}$ via $$r_i = \text{ArgLocalMax}_r[M(x_i, r)] \quad (1)$$

where $M(x_i, r)$ is a medialness function. Medialness functions respond maximally when applied at the center $x_i$ of a gray-scale object and at a scale r proportional to the radius of the object. A medialness function that uses a weighted sum of five kernel convolutions can be used. The kernels are distributed along a centerline about $x_i$, and each kernel is a radial sampling of a binary center-on/surround-off kernel oriented normal to its centerline point. FIG. 5 is a 3D rendering of a vascular model with a set of kernels distributed about the vessel centerline. In FIG. 5, kernels 500 are radially distributed about vessel model 502. Each kernel is a radial sample of a center-on/surround-off binary filter oriented normal to the centerline of vessel model 502. The local radius that produces a maximum response from the weighted sum of these kernels defines the radius $r_i$ at a point $x_i$ on the centerline. The kernels are weighted da based on their distance from $x_i$ $$M(x_i, r) = \sum_{a=-2}^{2} d_a K(x_{i+at}, r) \quad (2)$$

The scalar t is chosen so as to space the kernels along the centerline proportionally to the estimated radius at the previous point $r_{i-1}$, i.e. $t=0.5 r_i$. The weights $d_a$ decrease linearly from $a=0$ and sum to one.

Two of the most important benefits to this approach to radius estimation are as follows. (1) The kernels cover a large extent of the tube, thereby providing additional insensitivity to image noise. (2) The kernels are fit to the spatial curve of the centerline, thereby reducing assumptions about the local shape of the tube. Tests that demonstrate the method estimates centerlines in noisy images in seconds with sub-voxel accuracy and with insensitivity to the position of the initial seed point $x_0$ and the initial radius $r_0$ estimate have been performed. (See Aylward et al., "A Comparison of Methods for Tubular-Object Centerline Extraction," IEEE Transactions on Medical Imaging, 21(2):61-75 (2002).) These centerlines and radius representations are the basis of the present registration process.

III. Liver Studies Illustrating Success of Hierarchical Vessel-Based Registration As illustrated above in FIG. 4, the subject matter described herein includes tissue surface modeling, registering tissue surface models with tissue surface image data, and combining tissue surface model-to-image registration with vascular model-to-image registration. The following sections illustrate examples of blood vessel and tissue surface modeling and model-to-image registration for using human liver image data as an example.

A. Pre-Operative Liver Surface and Vessel Extraction

Figure 6A:
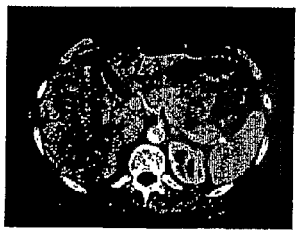
FIGS. 6A-6C are CT scans of a liver.
Figure 6B:
Figure 6C:

The input to the present liver surface and vessel extraction methods can be any suitable image in which vessels, tissue surfaces, and features of interest are identifiable, such as CT or MR scans. The CT scanner used in the examples described herein is a Siemens Sensation 16 multi-detector unit. Liver scans are acquired 30 and 60 seconds after contrast injection to help distinguish portal from hepatic vessels. FIGS. 6A-6C illustrate CT images of the liver used in this example. More particularly, FIG. 6A illustrates one slice from a portal-phase contrast CT scan. FIG. 6B illustrates one slice of a hepatic-phase contrast CT scan acquired 30 seconds after the portal phase scan. FIG. 6C illustrates one slice from a subtracted 3D VIBE MR scan. Voxel size is 0.56×0.56×1.5 mm. For MR imaging of liver parenchyma and vasculature a 3D VIBE sequence on the Siemens 1.5T Sonata MR scanner was used. This 17-second contrast-enhanced acquisition sequence can capture liver volume and vasculature at 0.6×0.6×2.5 mm. A pre-contrast VIBE scan from a VIBE scan acquired 23 seconds after gadolinium contrast injection (FIG. 6C).

The semi-automated liver surface segmentation process is a sequence of connected component and morphological operations (Aylward 2002a) that has been shown to be faster and more accurate than hand segmentation (Weeks 2001). Specifically, (1) from a user-specified starting point and using lower and upper intensity thresholds specified by the user, the voxels spatially connected to the starting point and having intensities within the thresholds are identified (this is the standard connected components technique). (2) That component is pruned via erosion using a spherical operator to remove sections that are only connected by thin strands to the main components. The main component is subsequently dilated by the same amount to return it to its original borders (minus its clipped regions). (3) The main component is then dilated using a spherical operator to fill-in small holes and again subsequently eroded by the same amount to return it to its original borders (minus its holes and clipped regions). (4) A Finite Element Quad-Mesh is fit to the segmented liver using methods in the NLM's Insight Toolkit. All liver segmentations are performed using the hepatic-phase CT data with 200 and 400 HU as the thresholds and 1.2 cm as the radius of the erosion and dilation operators. Sometimes it is necessary to edit the resulting segmentations, for example, to exclude the inferior vena cava. On CT scans of water filled balloons and surgical gloves, the present semi-automated process requires approximately 1 minute per item and estimates the volumes to within 10% of ideal; on the same data, hand contouring requires up to 15 minutes per item and averages 20% error (Weeks 2001). This semi-automated segmentation process, while effective, is not critical to the success of the present system; manual contouring could be used to generate the surface model needed for feature-image registration. However, the present semi-automated method has been used to segment livers from over 20 subtracted VIBE scans and 80 liver CT scans with excellent results.

Accurate 3D vessel segmentations have been performed using the method described above: Over 80 liver CT, over 20 liver VIBE MR, and over 150 head MRA scans have had their vessels segmented using the present method. As described above, the segmentation method includes dynamic-scale centerline extraction followed by adaptive radius estimation. Monte Carlo simulations have been conducted to measure the present vessel extraction method's speed, accuracy, and dependence on its initial parameter values (Aylward 2002a). Those analyses demonstrate the level of detail and accuracy that can be expected from the present pre-operative vessel models. They are summarized below.

To evaluate centerline extraction accuracy, a mathematical model of a tortuous vessel was created and three different magnitudes of Gaussian noise were added to its image data. The vessel had a radius of 4 voxels at its ends and 0.5 voxel at its middle. At its middle it branched. The branch was optimally difficult—each branch was identical and only spanned one voxel. For each level of image noise, the present dynamic-scale ridge traversal method was applied using different initial scales and 200 randomly chosen starting points within the object. Average time to extract 20 voxels of centerline was about 0.3 seconds. At the low and medium levels of noise, average centerline error was less than one voxel, maximum error was about two voxels, 90% of the centerline points were with in one voxel of ideal, and the branch point was traversed 60-80% of the time. Regarding automation, the accuracy of the centerline extractions was not statistically significantly affected by the starting parameter values (initial scans and starting points).

To verify the centerline extraction method on clinical data, tests were performed using 300 extractions of a small (radius ~1 voxel) and tortuous vessel in intracranial time-of-flight MRA data were performed using. Seed points to designate the vessel of interest were randomly chosen within two radii of the vessel. No two extractions of the centerline of interest differed by more than $\frac{1}{10}^{th}$ of a voxel.

To evaluate radius estimation accuracy and consistency, another vessel with multiple branch points was simulated. Three different levels of Gaussian noise were added to its image data. At each noise level, 300 random centerline extractions were performed. The average radius estimation error was less than ½ voxel, maximum error was approximately one voxel, and ~80% of the estimates were within ½ voxel of ideal.

Capturing vascular movement is critical to capturing deformations internal to the liver, and the level of detail provided by the present pre-operative models is well beyond what has been used by others. Surface models alone are insufficient since only a small segment of the liver surface is captured in each ultrasound scan, and it may be difficult to correlate surface movement with deformations internal to the liver. However (King 2001a,b) limited vessel models to manually specified centerlines of the major portal vein and the inferior vena cava, and (Porter 2001) used simple thresholding to find bright voxels indicative of vessels in MR and Doppler ultrasound.

Figure 7A:
FIGS. 7A-7C illustrate exemplary liver vessel models extracted using a vessel modeling technique according to an embodiment of the subject matter described herein.
Figure 7B:
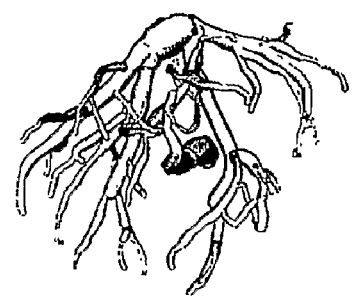
Figure 7C:
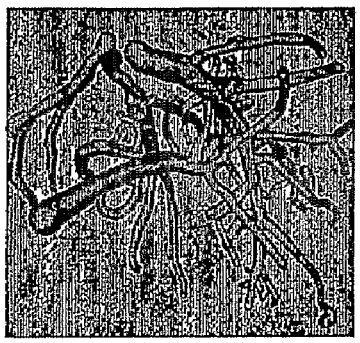
Figure 7D:
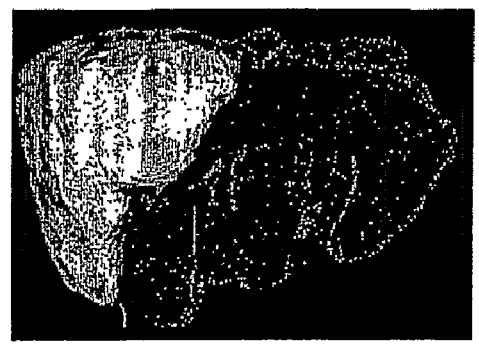
FIG. 7D illustrates a liver, its vessels, and a right lobe segmented from a CT image using blood vessel and tissue surface modeling technique according to an embodiment of the subject matter described herein.

Examples of the application of the present liver surface and vessel segmentation methods are given in FIGS. 7A-7D. More particularly, FIG. 7A illustrates a vessel tree extracted from a portal-phase contrast CT scan. FIG. 7B illustrates a vessel tree extracted from a hepatic phase contrast CT scan. FIG. 7C illustrates a vessel tree extracted from pre/post 3D VIBE MR sequences. FIG. 7D illustrates a liver, its vessels, and right lobe segmented from a CT scan. The 3D visualizations illustrated in FIGS. 7A-7D may be useful for partial liver transplant planning. The other source of data in ultrasound annotation: the intra-operative ultrasound data, will now be discussed.

B. Intra-Operative Ultrasound Acquisition

Target images to which the hierarchical model-to-image registration methods may be applied can be obtained from any suitable source. In one example, a Meduson Voluson 530D 3D ultrasound system was utilized to obtain ultrasound images of the liver for the present method. The strength of the Voluson 530 scanner is that it acquires 3D ultrasound scans without requiring the operator to perform a sweeping motion—the linear transducer internal to the probe is automatically swept to acquire the 3D data. Unlike the freehand 3D option on 2D ultrasound machines, these 3D scans are FDA approved for volume and other 3D measurements. Self-contained, automated 3D sweeping greatly simplifies the mental and physical demands placed on the clinician and reduces the risk of spatial errors.

One complication with the Voluson 530 is that scans require 7 to 15 seconds to be acquired. Given that the PLL-RFA patients are often not under respiratory control, 7 to 15 second scans are likely to suffer from intra-scan organ movement. A Volu son 730 scanner that offers sub-second scan times may be used to perform the scans.

Figure 8A:
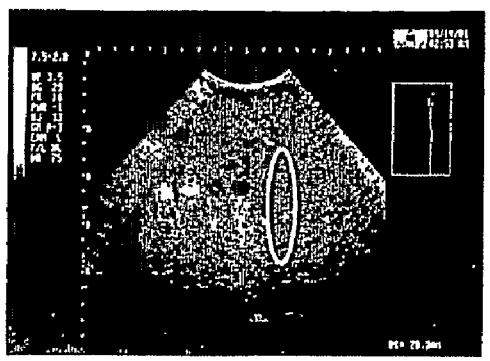
FIGS. 8A and 8B illustrate calibration images used to calibrate an ultrasound scanner for acquiring target image data.
Figure 8B:
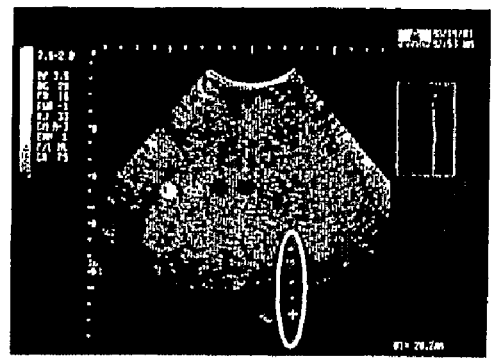

To measure the spatial accuracy of the present 3D ultrasound scanner, a Rammex RMI 403GS (Middleton, Wis.) calibration phantom (FIGS. 8A and 8B) was used. After Cartesian resampling by the Voluson system, 3D scans captured distances within one voxel throughout their entire volume—accuracy did not vary for deep or off-center targets. Nevertheless, in liver acquisitions, as the ultrasound pulses pass through heterogeneous tissues, spatial distortions may occur. These distortions, however, will have equal effect on the apparent position of the needle, liver surface, and liver vessels within the ultrasound data. Since the present methods are primarily concerned with the relative locations of these objects, the ultrasound distortions should have minimal effect on physician performance or accuracy when using ultrasound annotation.

The present example did not involve the acquisition of Doppler ultrasound images. The Voluson 530 produces very poor quality Doppler ultrasound images. Doppler ultrasound images have been determined to be unacceptable for clinical use, and review has showed that the quality and quantity of the vessels captures with Doppler is less than what is available in its b-mode images. In a manufacturer demonstration, the GE Voluson 730 provided significantly better 3D Doppler images. However, it is believed that the present method would be more broadly applicable if 3D Doppler images weren't required since not all 3D acquisition techniques can provide them, e.g., the popular Stradx software for creating 3D ultrasound images cannot create 3D Doppler images.

Ultrasound probe tracking cannot account for organ changes between pre- and intra-operative image acquisitions, intra-operative patient movements, internal organ movement, or organ deformations; however, the present method will track the 3D ultrasound probe when ultrasound data is acquired and then use the tracker data to initialize the registration of the ultrasound data and the pre-operative models. The tracker data provides rigid transforms that capture relative probe movements between subsequent ultrasound scans. That rigid transform is compounded with the previously resolved image transform to initialize the next image registration process. One exemplary tracker suitable for use in tracking an ultrasound probe is a Flock-of-Birds magnetic tracker (Ascension Technologies). To reduce the ultrasound probe's interference of the magnetic sensor, the sensor is fixed to the end of a rigid, 15.5" long piece of plastic that has an extruded triangle shape. At the other end, an aluminum ring passes through the plastic and can be tightened around the ultrasound probe handle. This setup has been determined to be particularly stable and broadly applicable. This setup, however, requires calibration of the relationship between the sensor and points in the ultrasound data. For tracker to ultrasound data calibration, a 5×5×5 cm pyramid-shaped wireframe object was constructed. It is placed in a bucket of water, and three or more tracked 3D ultrasound scans are acquired. The location and orientation of the object in each scan is determined using a generalized Hough transform (Ballard 1981). The present method solves (using a squared-error minimization technique initialized with expected values) for the transformation matrix that can be compounded with each tracker position to align their object representations. Repeated calibrations of the same probe/sensor setup were performed. For a sensor to probe tip distance of 338.4 mm, the standard deviation of four repeated calibrations was 0.145 mm and the maximum difference from the mean was 0.168 mm. Another possible source of magnetic tracker error is field deformation due to metal moving near the sensor. The present studies indicate that this error may be significant. In particular, a tracker sensor sitting on a surgical bed beside a patient will appear to move as much as 11 mm when a 24-gage biopsy needle is moved near it. Such additional uncertainty in registration initialization adds to the time required perform the image registration process. It may therefore be desirable to use an optical tracker to track the ultrasound probe and thereby accurately initialize registration. Using an optical tracker will allow focus on the primary purpose for image registration in ultrasound annotation, i.e., accounting for liver deformation due to patient movement, organ movement, breathing, needle pressure, etc. that external tracking cannot capture.

C. The Feature-Image Match Metric

The present registration metric quantifies how well a transform aligns liver surface and vessel models from pre-operative data with intra-operative ultrasound images. The present metric uses the physics of ultrasound acquisition when specifying the type of measures to be made in the ultrasound images. For example, since vessels appear as dark tubes in 3D ultrasound images, when a vascular model is aligned with an ultrasound image, the centerline points of the model will map to dark voxels in the image. Similarly, organ surfaces form bright or high gradient surfaces in ultrasound images, dependent on the orientation of the ultrasound probe with respect to the orientation of the surface. However, occluded regions are also commonly present in ultrasound data, and vessel/surface features will not be visible in those regions. Therefore, prior to initiating intra-operative registration, it is necessary to identify occluded regions and exclude them from influencing the registration process.

Figure 9:
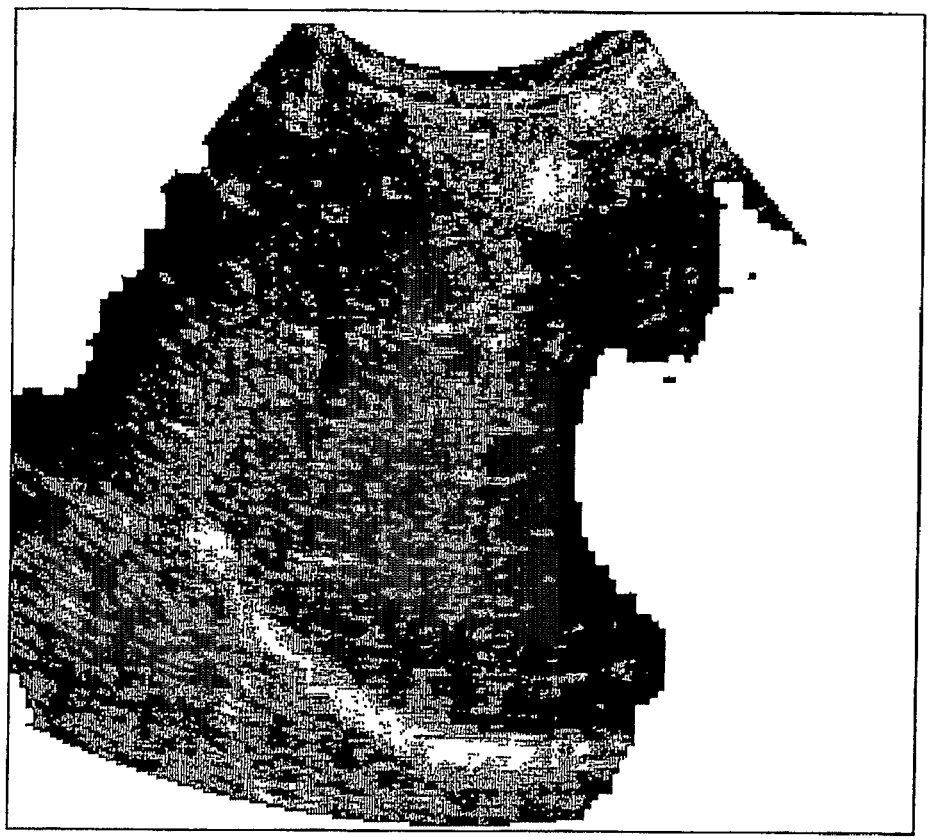
FIG. 9 is a liver ultrasound scan illustrating the result of identification of occluded regions in the ultrasound scan according to an embodiment of the subject matter described herein.

Occluded region identification: The present subject matter includes a method for rapid identification of occluded regions in ultrasound images. The occluded regions are designated as don't care regions so that features that map into those regions will neither dilute the match metric nor create false local metric maxima. The primary emphasis during occluded region masking is speed; underestimating an occluded region is allowed since the present registration method is insensitive to missing features (Aylward 2003). The present occluded region masking method operates by down-sampling the 3D ultrasound images from 256×256×256 to 64×64×64 (requires 0.64 seconds) and then convolving that sub-sampled image with a 1D Gaussian derivative kernel oriented approximately along the ultrasound wave propagation direction (via table lookup). The intensity and gradient magnitude are then thresholded to identify points within the occluded region. Thresholds were chosen based on observations from multiple 3D ultrasound scans; the thresholds have worked on every subsequent scan without modification. The resulting mask is then up-sampled to 256×256×256 using nearest-neighbor interpolation. Convolution, thresholding, and up-sampling requires 1.86 seconds. Total computation time is ~2.5 seconds. This processing was implemented using ITK, the National Library of Medicine's Insight Toolkit for Medical Image Segmentation and Registration: www.itk.org. ITK provides multi-threading and data streaming—with the requested dual-processor machine, the computation time should be reduced by 40-50%. Results are illustrated in FIG. 9. More particularly, FIG. 9 illustrates a 3D mask computed using the method described in this paragraph. The computation of the 3D mask in FIG. 9 required 2.505 seconds. The robustness of the present registration process allows for the underestimation of the occluded region. Emphasis was therefore placed on speed.

Vascular Feature-Image Match Metric: One exemplary metric suitable for use with the subject matter described herein quantities the match between pre-operative vascular models and the intra-operative ultrasound image data. Again, the present implementation focuses on vascular features since they have received the least attention by other groups, and yet they may be best at capturing deformations internal to the liver. The vascular feature-image match metric is given by:

$$F(T) = \frac{1}{\sum_{i=1}^{n} w_i} \sum_{i=1}^{n} w_i I^{inv}_{kr_i}(T(x_i)) \tag{3}$$

Figure 10:
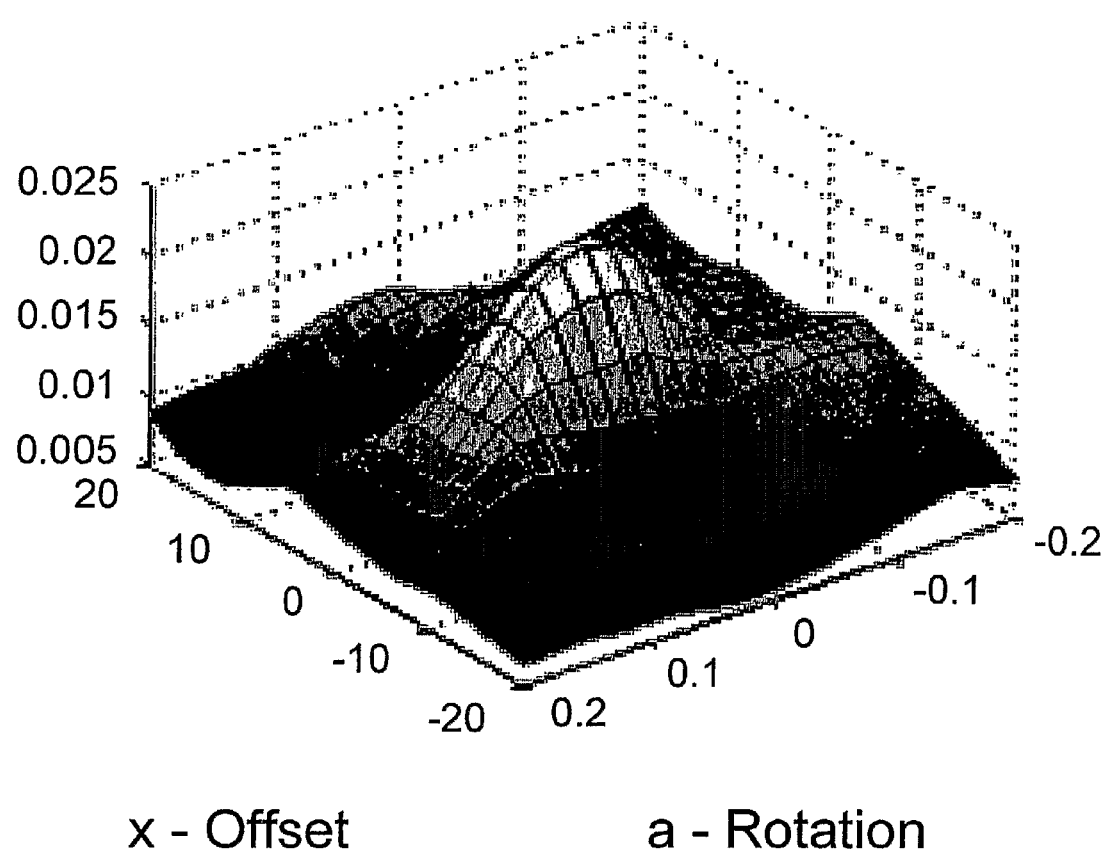
FIG. 10 is a graph of changes a in registration metric for a range of x offsets and xy plane rotations given vessels from a liver MR scan applied to a 3D ultrasound scan according to an embodiment of the subject matter described herein.

For a given deformable transform function T, the metric is controlled by the sampling of the vessels' centerlines (n samples designated $x_i$), the local scaling ($kr_i$) of the intensity-inverted ultrasound image data ($I^{inv}$) at each transformed centerline point, and the weighting ($w_i$) of each centerline point. The data is scaled (blurred using a Gaussian having a standard deviation of $kr_i$) to increase the conspicuousness of tubular intensity structures of radius $r_i$ (Aylward 2002a, Lindeberg 1994). The intensities in the ultrasound image are inverted to make the vessels appear brighter than the background, thus the metric is maximal when the vessel models are registered with the image. The weightings are changed during registration to first favor large vessels and then to include smaller vessels. Not portrayed in this equation is the additional constraint that any centerline point that is transformed into an occluded region is not included in the calculations. An analysis of these parameters is provided in (Aylward 2001, 2003). FIG. 10 is a graph of the metric for +/−20 voxels of x-offset and +/−0.2 radians of xy-plane rotation, given the vascular model in FIG. 7C from the MR scan in FIG. 6C and the 3D ultrasound data with the masked occluded region in FIG. 9. More particularly, FIG. 10 illustrates the change in metric value for a range of x offsets and xy plane rotations given vessels from a liver MR scan applied to a 3D ultrasound scan. The zero coordinate was determined by an initial registration using vessel based feature-image registration. The metric has a global maximum at registration (the zero coordinate) and no erroneous local maxima for a wide range of offsets and rotations.

As will be described below, this metric is extended to include surface models and measures. Additional aspects of the physics of ultrasound acquisition will also be described.

D. Deformable Transform Optimization

In addition to using a vascular feature-image match metric, the present implementation includes a coarse-to-fine deformable registration. Traditionally coarse-to-fine registration is implemented using an image pyramid, a sequence of sub-samplings. However, by using deformations at one scale as a prior for deformations at a finer scale, for every point in an image, the underlying assumption is that the objects throughout the image have equal coherence across those scales; yet, objects exist at different scales in images. For the present application, blood vessels inherently provide a natural coarse-to-fine hierarchy as tree structures. In the liver the portal and hepatic vessels form two distinct trees. The accuracy of the present tree formation process isn't critical, but has been demonstrated to be over 98% accurate as evaluated by comparison to x-ray angiograms by expert radiologists (Bullitt 2001b). These vascular tree structures are used to localize and scale the present system's coarse-to-fine registration process.

As illustrated in FIG. 3, one exemplary deformable transform optimization process includes three steps. The first step is global rigid registration using a vessel-image metric (Aylward 2001, 2002a, 2003). The second step consists of a piecewise rigid registration process applied hierarchically from vessel tree roots to leaves. The third step is a piecewise non-rigid deformation process that is also applied from vessel tree roots to leaves. The two last steps are unique, and their use of the vessel hierarchy supports fast registration by eliminating the need to compute intra-operative image pyramids.

Rigid registration: The present deformable registration strategy is initiated by solving for a global rigid transform that maps the pre-operative models into the intra-operative ultrasound data (Aylward 2001, 2002a, 2003). A unique property of the present method is that it limits vessels to inducing registration updates in their normal directions. Furthermore, the iterative updates of the rigid transform are adjusted for the orientation bias of the vessels. For example, if most of the vessels in the network have a horizontal orientation, the total vertical update they induce is down-weighted so that horizontal alignment updates can have equal force. This registration process achieves consistent, sub-voxel convergence from 0.2 radians of mis-rotation and 20 voxel offsets in 2-3 seconds for MR to ultrasound registration. The present rigid registration implementation, involving only vasculature, operates as follows.

A matrix $N_i$ is defined to specify the plane normal to each transformed vessel centerline point. For the vessel model points, that matrix is defined as $$N_i = T(n_{1i}) \circ T(n_{1i}) + T(n_{2i}) \circ T(n_{2i}) \tag{4}$$

where $\circ$ denotes the outer product operator, and the $n_{ji}$ are the directions normal to the vessel centerline at $x_i$.

To limit a vessel point to inducing changes in its normal directions, the scaled image gradient is projected onto its normal plane $$\nabla I_{kr_i}^N(T(x_i)) = N_i \nabla I_{kr_i}(T(x_i)) \tag{5}$$

To remove the global orientation bias, the spread of the normal planes is calculated for the subsampled centerline points as a global bias matrix $$B = \sum_{i=1}^{n} w_i N_i \tag{6}$$

Then each projected gradient is corrected for the global orientation bias by multiplying it by the inverse of the global bias matrix $$\nabla I_{kr_i}^B(T(x_i)) = B^{-1} \nabla I_{kr_i}^N(T(x_i)) \tag{7}$$

Even though each normal plane $N_i$ is of reduced rank (3×3 matrix of rank 2), the bias matrix B is invertible as long as all of the vessels in a network are not parallel. The unbiased gradients from Equation 7 are then used to determine updates to transforms parameters that maximize the metric. For example, offset vector updates $\Delta o$ during registration optimization are defined as the weighted sum of the unbiased, projected gradients.

$$\Delta o = \sum_{i=1}^{n} w_i \nabla I_{kr_i}^B(T(x_i)) \tag{8}$$

Piecewise rigid registration: After global rigid registration, a rigid transformation is calculated to refine the position of each vessel, in a hierarchical manner. First, if a root of a vascular tree overlaps with the ultrasound image after global rigid registration, its position and orientation (independent of other vessels) is refined using a rigid transform and the metric. Vessels spanning more than 20 voxels are broken into 20 voxel segments. Second, each root's branches are registered rigidly with the image, one branch at a time, using the tree's parent-child hierarchy and using branch points as anchor points. Again, only those branches that were determined to overlap the intra-operative image, based on the global rigid transform, are used, and long vessel segments are broken into shorter vessel segments. For each branch, its rotation about its branch point is solved iteratively using the present vessel-image metric (Equation 3 and (Aylward 2001b, 2003)). Each branch's rotation is computed independently, and its descendants do not contribute to the metric. The weightings of the points in each branch's model ($w_i$ in Equation 3) decrease based on their distance from the branch point. A branch's translation is constrained to be along its parent. Specifically, the translation vector of the child is projected onto the tangent direction of its parent vessel at the branch point, and the amount of translation allowed is constrained by an "elasticity" property of the parent vessel; translation updates are dampened by how much a branch point has been translated from its initial location. Updates use a gradient ascent optimization strategy. While appearing complex, the multiple constraints involved reduce the complexity of the transformation's parameter space and thereby speed the registration process; this step requires only ~5 seconds.

Piecewise non-rigid of deformable registration: The piecewise non-rigid or deformable registration step parallels the rigid registration step. (1) The image gradient is computed at a scale proportional to the radius of the local vessel point and projected onto the normal of the vessel point to determine how that vessel point should move, as was done for rigid registration in (Aylward 2001, 2002b, 2003) (Equation 5). (2) To handle local image noise and avoid overly complex deformations such as folding, a "rigidity" coefficient that dampens vessel bending is added. Specifically, it dampens updates based on the difference between the initial curvature at a vessel point and the current curvature at that point. This rigidity coefficient varies along a vessel, proportional to the radius of the vessel (it and "elasticity" could also depend on the material properties of the vessel and liver, but such precision is unnecessary for image-driven registration). In the present implementation, this rigidity value is kept constant at every point, and the sampling rate along a vessel is used to accommodate the coefficient as the radius changes (Equation 3). (3) This process is applied starting from each root and spreading to their branches. Steps (1) and (2) closely resemble a deformable explicit snake that maximizes the integral of the scaled intensities it encounters and minimizes its internal/bending energy. By using a coarse-to-fine approach based on the vascular tree, this process requires only 10-15 seconds.

Total deformable registration time is 20-30 seconds. Next, the model's transform is interpolated to transcribe pre-operative markings, such as desired PLL-RFA sites, into the intra-operative ultrasound data.

E. Desired PLL-RFA Site Transcription

Knowing how the pre-operative model deforms to fit the intra-operative data, the transform needed to transcribe desired PLL-RFA sites from the pre-operative data into the intra-operative data's overlay is estimated. In order to estimate the transform, a deformation field vector value D at a point x is estimated using the method in (Pennec 2003), i.e., using Gaussian interpolation of the update vectors $d_i$ at model points $x_i$ as follows $$D(x) = \sum_{i=1}^{n} d_i G_\sigma(x - x_i) \quad (9)$$

where the scale σ of the Gaussian function G is fixed at 2 cm.

Deformation field interpolation is an instance of deformation field regularization; this class of methods has been the focus of much research. Excellent iterative, large-deformation diffeomorphic field generation, and finite element model based techniques have been developed for deformation field regularization (Joshi 2000). These methods, however, tend to be dense field techniques—it is necessary to solve for many (often all of the) points in a deformation field to determine the deformation field at any particular point.

Equation 9 has been used (King 2001a,b; Pennec 2003) for intra-operative deformation field interpolation since it is only necessary to evaluate it at the PLL-RFA points to determine how to translate them into the ultrasound's coordinate system. This computation is fast and produces acceptable results under the assumption that the deformations are small and smooth—this is likely the case for ultrasound annotation for minimally invasive procedures such as PLL-RFA. Nevertheless, there are problems with Equation 9; it lacks consideration of the fact that model deformation vectors $d_i$ only capture the normal-direction components of the underlying deformation field—by design, they lack the tangential component (Equations 4-8). The present solution is applicable to many of the model, active-contour, active-surface, active-shape and sparse-field deformation strategies that limit model updates to normal directions.

Regardless of this limitation, however, the present preliminary implementation uses this equation to produce fast, consistent, and accurate results using phantom and clinical data. They are discussed next.

F. System Evaluation 1: Consistency of Rigid Registration given Clinical Data

The following test demonstrates the present system's ability to consistently rigidly register the exact types of data that it will encounter in the proposed work and when used in a clinic. As detailed in the previous section, global rigid registration is the initial step in the present deformable registration process. This evaluation begins by estimating liver motion due to breathing to determine how much liver displacement is likely to occur during a procedure. That estimate is used to generate Monte Carlo runs for quantifying the consistency of MR to ultrasound registration.

Liver motion due to breathing is the likely source of much of the intra-operative liver displacement. A portal-phase CT scan at maximum breath inhale and a hepatic-phase CT scan at maximum exhale was acquired. The vessel models from the portal scan were modeled, and those models were then registered with the hepatic scan using the present rigid registration strategy. The resulting transform parameters are given in Table 1. On inhale, the liver translates to the posterior and rotates to the inferior along a sagittal course. Total movement is about 1 cm and 0.09 radians.

TABLE 1

The parameters of the transformation generated to register a portal-phase CT scan's vascular model with a hepatic-phase CT scan. The portal-phase scan is a maximum inhalation scan and the hepatic-phase scan is a maximum exhalation scan. These parameters are consistent with the 1-2 cm displacements reported by others (King 2001a, b) and (Herline 1999).

| Parameter | Value (voxel/radians) |
|---|---|
| x-offset | 1.303 |
| y-offset | −10.953 |
| z-offset | 0.167 |
| xy-rotation | 0.012 |
| xz-rotation | 0.022 |
| yz-rotation | −0.058 |

Figure 11A:
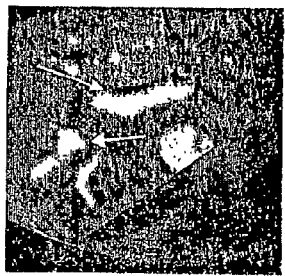
FIGS. 11A and 11B show ultrasound scans overlaid onto different slices of an MR scan according to an embodiment of the subject matter described herein.
Figure 11B:
Figure 11C:
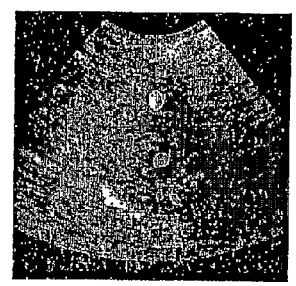
FIG. 11C illustrates vessel models from an MR scan overlaid on an ultrasound scan according to an embodiment of the subject matter described herein.

Monte Carlo experiments were then conducted to measure the consistency with which MR vascular models and ultrasound data could be rigidly registered given liver breath motion. A patient was scanned using the 3D VIBE MR sequence and three days later, two 3D ultrasound scans were acquired—one on inhale and one on exhale. A liver vasculature model was extracted from the MR scan and registered with each ultrasound scan. Each registration was roughly initiated by hand (in the clinic, an optical tracker would provide this initialization) and the present vascular-model-to-image rigid registration method was applied to refine those registrations. Each rigid registration required less than 3 seconds and appeared to be accurate despite the fact that the patient's liver was not cirrhotic and therefore contained deformations (FIG. 11). More particularly, FIGS. 11A and 11B illustrate two ultrasound scans overlaid on two different slices of an MR scan. These scans were aligned by registering a vascular model from the MR scan with each ultrasound scan. Vessel and liver surface correspondences are indicated by arrows. In FIG. 11C, vessel models from the MR scan are overlaid on an ultrasound scan. Shadowing is evident in nearly one half of this slice, but registration was consistent as illustrated in Table 2 below.

From this initial registration, Monte Carlo experiments were conducted; the registration of the MR vascular models to the ultrasound data was repeated given random initial misregistrations based on expected liver motion due to breathing, i.e., ±1 cm (~14 voxels) and 0.1 radians from Table 1. Results from the 97 successful of the 100 re-registrations are in Table 2.

TABLE 2

Re-registration Results

| Parameter | Std. Dev. (vxl/rad) | Max diff from mean (vxl/rad) |
| --- | --- | --- |
| x-offset | 0.374 | 1.176 |
| y-offset | 0.741 | 2.865 |
| z-offset | 0.715 | 2.682 |
| xy-rotation | 0.012 | 0.049 |
| xz-rotation | 0.010 | 0.031 |
| yz-rotation | 0.011 | 0.038 |

The proposed extensions are expected to reduce the failure rate to zero and to improve both accuracy and consistency. In the evaluation described in the next section, the registration method's accuracy is evaluated.

G. System Evaluation 2: Phantom Data Registration Accuracy

These preliminary studies quantify the accuracy with which tumors, visible in CT can be transcribed into ultrasound data using a rigid vascular registration method, even when a needle is present in the ultrasound data. These studies involved a gelatin phantom containing simulated vessels and tumors and a biopsy needle.

Figure 12A:
FIG. 12A is a computer image of a tub of gelatin and soba noodles used to test a method for liver vessel registration according to an embodiment of the subject matter described herein.
Figure 12B:
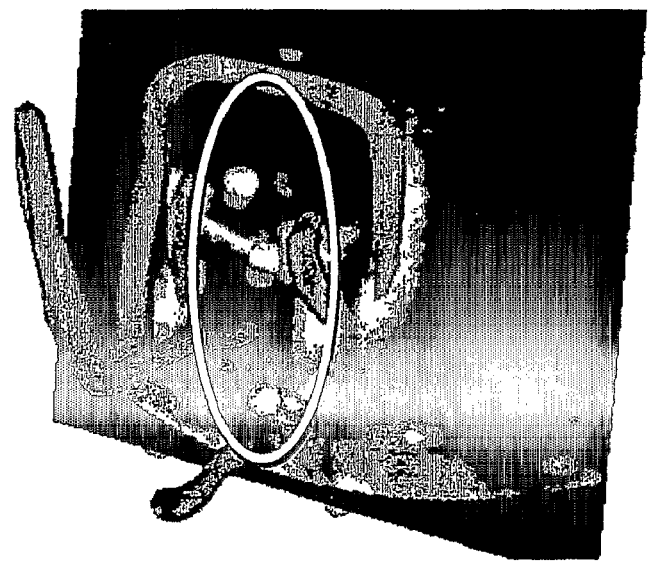
FIG. 12B is a computer image illustrating results of vascular registration of the image illustrated in FIG. 12A.

Specifically, a tub of gelatin containing soba noodles and four 5×5×5 mm targets was scanned in a CT system using a standard liver protocol. A model of the vessels/noodles was extracted from that scan. An ultrasound scan with an RFA needle inserted through the center of the tub was then acquired. The CT vessel models were roughly rigidly registered with that ultrasound scan using a calibrated magnetic tracker. The centers of mass of the four targets were calculated in each scan The mean distance between those centers across the roughly registered scans was 8.8 mm and the max distance was 9.8 mm. The vascular registration system was then used to refine the alignment of the CT model with the ultrasound data. This registration required ~2 seconds. The mean distance between corresponding targets was reduced to 2.0 mm and the max distance was reduced to 2.2 mm (FIG. 12). More particularly, FIG. 12A is an image of the tub of gelatin and soba noodles. It was determined that a tub of gelatin and soba noodles has CT properties within a few HU of liver CT properties. Vessels were extracted from Cr scan and then registered with the ultrasound scan. In FIG. 12B, after vascular registration, mean distances reduced to 2 mm and maximum distances less than 2.2 mm (dark=CT vascular model and targets, light=ultrasound based targets). These results are well within the 5 mm required for PLL-RFA. Admittedly, registration accuracy is not the sole determinant of needle placement accuracy during PLL-RFA; nevertheless, the proposed studies involving deformable transforms and clinical PLL-RFA data are justified.

H. System Evaluation 3: Clinical Data Deformable Registration

Figure 13A:
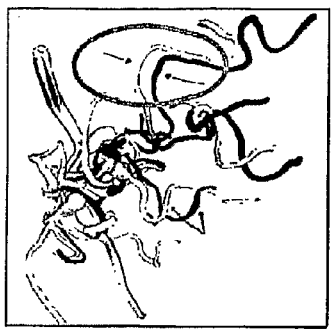
FIG. 13A is a computer image illustrating the results of global rigid alignment between a vascular model from a post-operative scan directly with a pre-operative scan according to an embodiment of the subject matter described herein.
Figure 13B:
FIG. 13B is a compute image illustrating the results of piecewise rigid registration between a vascular model from a post-operative scan with a pre-operative scan according to an embodiment of the subject matter described herein.
Figure 13C:
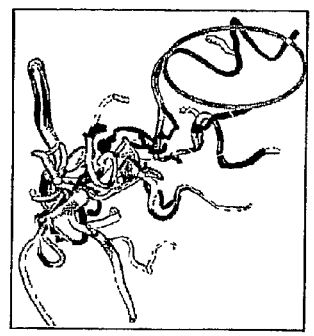
FIG. 13C is a computer generated image illustrating the results of piecewise deformable registration of a vascular model from a post operative scan with a pre-operative scan according to an embodiment of the subject matter described herein.

This section illustrates the performance of the present vessel-tree-based hierarchical, deformable registration strategy using clinical MRA data. Two clinical sets of data have been evaluated in detail: (a) intra-cranial MRA data acquired pre and post arteriovenous malformation embolization and (b) liver CT data acquired six months apart. Each deformable registration required 20-30 seconds and provided sub-voxel accuracy at the vessel model points. The three steps of deformable registration are illustrated for these data in FIGS. 13 and 14. More particularly, in FIGS. 13A-13C, two vessel networks are shown. The dark grey (post operative) vascular models are being deformably registered with the MRA image data used to generate the light grey (pre-operative) vascular models. The light grey models are not used in the registration. They are only shown for reference. FIG. 13A illustrates the results of globally rigidly aligning a vascular model (dark grey) from a post-operative scan directly with a pre-operative scan (not shown-instead its vessel are shown by light grey to reveal registration accuracy). In FIG. 13B, the results from piecewise rigid registration are illustrated. In FIG. 13C, the results from piecewise non-rigid registration are illustrated. In FIG. 13C, the circles indicate an area of large deformation. Average distance between the vascular networks is sub-voxel.

Figure 14A:
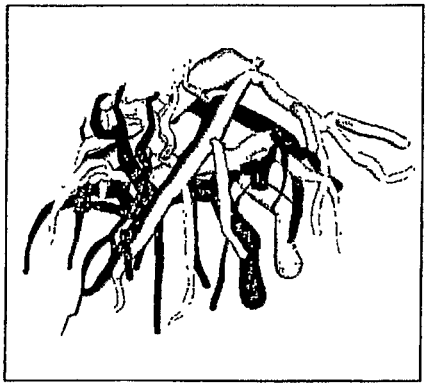
FIG. 14A is a computer image illustrating liver vessels from two CT scans taken six months apart before registration.
Figure 14B:
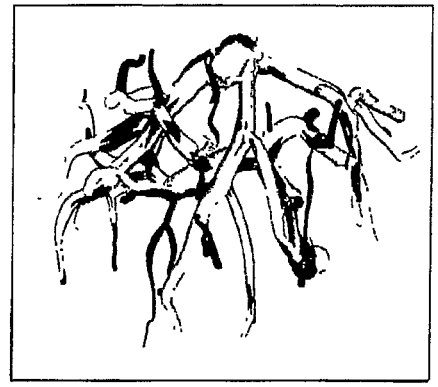
FIG. 14B is a computer image illustrating liver vessels from two CT scans after deformable registration according to an embodiment of the subject matter described herein.

In FIGS. 14A and 14B, liver vessels from two CT scans taken six months apart are shown. Two vessel networks are shown, but the dark gray vascular model is being deformably registered with the CT image data used to generate the light grey vascular model. FIG. 14A illustrates the model and image before registration. FIG. 14B illustrates the image and vascular model after deformable registration. In FIG. 14B, the mean distance between the deformed and the data's actual vascular network is 0.66 mm. The time required for registration is less than 30 seconds.

IV. Combined Hierarchical Vessel-Based and Tissue Surface Registration Methods

A. Research Design and Methods

The success of the implementation described above car be enhanced by incorporating principled extensions and conducting thorough validations. These developments and evaluations will use data from percutaneous liver lesion radio frequency ablation procedures (PLL-RFA). The specific aims are 1. To extend the preliminary, vessel-based deformable registration implementation to include surface information when transcribing desired RFA sites from pre-operative liver CT/M R images into 3D ultrasound images taken during PLL-RFA procedures.
2. To extend the ultrasound annotation system from Aim 1 to consider aspects of the physics of liver surface and vessel deformation. The present system embodies a philosophy that is simple to implement and that will increase the accuracy of point transcription for ultrasound annotation and for many other deformable registration methods.
3. To extend the ultrasound annotation system from Aim 2 to consider aspects of the physics of ultrasound acquisition. This extension tunes the intra-operative feature-image match metric to consider additional characteristics of the appearance of organ surfaces in ultrasound data.
4. To validate these implementations using clinical, retrospective, PLL-RFA data and PLL-RFA accuracy requirements.

Central to these developments and evaluations is the clinical PLL-RFA data that will be recorded and then used retrospectively. Via informed consent, pre- and post-operative MR or CT scans and intra-operative 3D ultrasound scans will be collected from 20 patients per year. The first five patients enrolled each year will be used for system development; the other 15 will be reserved for the evaluations. Therefore, at the end of three years, 15 patients' data will be available for training and 45 for testing. They will be grouped and made available from a web site as such. Details regarding the pre-operative MR/CT and intra-operative 3D ultrasound are described below.

Pre-operative CT/MR: It is necessary to acquire MR/CT scans of PLL-RFA patients to form pre-operative liver vessel and surface models to be used during registration. Most PLL-RFA patients come from outside referral, and electronic access to their prior CT/MR scans is generally not available. Randomly, but possibly modified by consent and health status, such as creatine levels, half of the patients will be assigned to receive a pre-operative MR and half will receive a pre-operative CT.

All CT scans will be acquired on a Siemens Sensation 16 multi-detector CT unit using a liver donor evaluation protocol. The portal and hepatic phase scans are acquired 30 and 60 seconds after contrast injection to capture portal and hepatic vessels details respectively. These scans are registered to generate a model that contains both vascular networks. These scans contain approximately 512×512×280 voxels with a voxel size of ~0.56×0.56×1.5 mm.

All MR scans will be acquired on a Siemens Sonata 1.5 T MR unit using a 3D VIBE sequence. This high gradient, 1.5 T magnet supports fast and detailed 3D and thin-slice images. The VIBE sequence is a T1 weighted 3D Flash breath-hold technique. Three-dimensional Fourier transform GRE imaging has potential advantages over 2D imaging. In comparison with traditional 2D GRE sequences, properly structured 3D GRE sequences have the capacity to provide thinner sections, no gaps, fat saturation, higher SNR, and comparable image contrast in the same breath-hold time frame. The VIBE sequence has TR=4.78 ms; TE=2.27 ms; FA=10; slab thickness=80 mm; effective slice thickness=2.5 mm; matrix size=195×256; FOV=320 mm; imaging time=20 to 23 seconds. Data can be acquired transverse and dynamically (pre-contrast, arterial phase, early portal venous phase and late portal venous phase) with a single dose of gadolinium. A pre-contrast scan is subtracted from a late portal venous phase image to emphasize vascular detail. These images cover the liver in a 512×512×200 voxel volume with contiguous ~0.6× 0.6×2.5 mm voxels.

A potential problem with abdominal MR is spatial distortion; however, since it is only necessary to capture the relative relationship between the liver's surface and vessels and the desired RFA sites in the MR data, if the MR distortions are not locally severe, it is not necessary to correct for them—deformable registration with the ultrasound data will still be valid—the relative locations of the image features will still be maintained. In the unlikely event that MR distortion is not continuous and severely distorts the relative location of objects in the MR scan, the proposed studies will be restricted to the use of CT. This is a reasonable fallback position, but the subject matter described herein can be used with MR images.

Intra-operative 3D ultrasound: 3D ultrasound scans will be acquired during PLL-RFA procedures: for each designated tumor one scan will be collected prior to needle insertion, two scans will be collected after needle insertion while en-route to the tumor, and one scan will be collected immediately prior to ablation initiation. It is preferable to use an ultrasound spacer on thin patients so that a larger portion of the liver surface near the ultrasound probe is captured and available for registration. Also, both b-mode and Doppler images will be acquired to compare their vascular detail and effect on registration performance in Aim 4. A GE Voluson 730 ultrasound machine may be used for these acquisitions. Compared to a Medison Voluson 530D, the GE 730 offers reduced (sub-second versus 7-15 second) scan times and Doppler capabilities. Faster scan times will reduce the amount of intra-scan organ movement that would degrade registration accuracy and consistency. Doppler scans are likely to provide improved vascular detail leading to improved registration accuracy. All scans are automatically stored in isotropic Cartesian coordinates using ~0.6×0.6×0.6 mm voxels. DICOM will be used to push each scan to a workstation.

As with MR, spatial distortions may occur in ultrasound images; however, also as with MR distortions, these distortions are not likely to disturb the relative location of objects in the images and therefore will have minimal effect on deformable registration performance. The pre-operative models will be registered directly with the ultrasound data, and the resulting desired PLL-RFA site overlay will maintain correct relative location.

As discussed above, ultrasound probe tracking cannot account for organ changes between pre- and intra-operative image acquisition, intra-operative patient movement, organ movement (particularly due to breathing), or organ deformations; however, the 3D ultrasound probe will be tracked when ultrasound data is acquired to initialize the registration of the ultrasound data and the pre-operative models by providing relative rigid transforms between consecutive ultrasound scans. The calibration protocol detailed above may be used. Since the present preliminary results demonstrate magnetic tracker interference from the RFA needle, an optical tracker may be more suitable for this purpose.

B. SA1: Ultrasound Annotation Using Model-image Registration

The present method is based on a consistent philosophy for the simultaneous consideration of vasculature and surfaces for model-to-image registration. The preliminary implementation focused on understanding and evaluating the potential of vasculature in intra-operative registration for ultrasound annotation. Vasculature has only received limited attention in intra-operative ultrasound registration (King 2001a,b; Porter 2002), but it has amazing potential: vasculature moves as the surrounding tissues move, are dense throughout the liver, and are clearly visible on ultrasound. Despite the strengths of vasculature, there is also a clear role for surfaces in registration; surface deformation ensures that estimating a deformation field only requires interpolation and not extrapolation to cover an organ.

In this Aim, an intra-operative ultrasound annotation system that embodies this philosophy will be implemented. The steps of the present ultrasound annotation method are (a) pre-operative CT/MR liver vessel and surface modeling, (b) pre-operative desired PLL-RFA site specification, (c) intra-operative deformable registration, and (d) intra-operative desired PLL-RFA site transcription. The basic processes and capabilities of these steps are described above. Here the modifications needed to incorporate surfaces into those processes are described.

(1) Pre-operative CT/MR Vessel and Surface Modeling: One exemplary liver vessel and surface modeling method is described and evaluated above and in (Aylward 1996, 2002a; Weeks 2001; Bullitt 20001a, b). This method provides accurate and consistent models. This method has been used to segment liver surfaces and vessels from MR and CT scans from over 100 potential partial liver donors. Vessels are represented by centerline points with radii. Surfaces are represented by quad-meshes.

(2) Pre-operative Desired PLL-RFA Site Specification: The interventional radiologist who will perform the PLL-RFA procedure will specify the desired needle destinations via point-and-clicks within the pre-operative image slices. These will be recorded using software developed for liver transplant planning. Many intra-operative factors determine the appropriate approaches to those sites, so only the sites and not the paths to those site can and will be specified on the pre-operative data.

(3) Intra-Operative Deformable Registration: The simultaneous and consistent consideration of vessels and surfaces is one of the innovations in described herein. Preliminary results demonstrate that considering vessels leads to a fast and accurate feature-image match metric; tumor locations are transcribed from pre-operative CT of a phantom into 3D ultrasound images in 2-3 seconds with maximum error of ~2.2 mm. Including surface features will support the localization of tumors near the liver surface where vessels are sparse. The clinical utility of this extension will be quantified in Aim 4.

Intra-operative deformable registration progresses in three steps: global rigid, piecewise rigid, and then piecewise deformable registration. Underlying all three is a common metric. Here the extension of the metric (Equation 3) to include surfaces is described. The corresponding extensions to the steps of registration are also described.

Vessel/Surface Feature-Image metric: The present surface registration metric assumes that surface model points map to bright voxels within the target image when the model and image are registered; just as vessel model points should map to the dark voxels in the image. The vessel-to-image match metric of Equation 3 is augmented to become a combined vessel/surface-to-image metric as follows:

$$F(R, o) = \frac{1}{\sum_{i=1}^{n_{Vessel}} w_i} \sum_{i=1}^{n_{Vessel}} w_i I_{K\vec{n}}^{inv}(T(x_i)) + \frac{1}{n_{Surface}} \sum_{i=1}^{n_{Surface}} I_{\sigma_s}(T(x_i)) \quad (10)$$

All surface points are considered equally important, so no surface point-specific weights are used. Additionally, the ultrasound intensities at transformed surface points are all measured at scale $\sigma_s=1$ mm, to dampen image noise (~2× speckle size). Not shown in Equation 10 (or Equation. 3) is the fact that a "don't care" mask is used. As described above, the present occluded region masking method identifies large, dark, "don't care" regions within an ultrasound scan in 2.5 seconds. Any model point mapping into those regions of occlusion is not considered in the metric or subsequent transform parameter update computations. Using this metric, global rigid, piecewise rigid, and piecewise deformable registrations are performed as follows.

Global rigid registration: The strengths of the present vessel registration process are maintained in the present vessel/surface registration process. (1) Vessels and surfaces are limited to inducing registration updates in their normal directions. (2) Parameter updates are adjusted to remove any biases resulting from the vessels and surfaces having a dominant orientation. As defined in Equation 4 above and in (Aylward 2001, 2003), a matrix $N_i$ is used to encode the normal directions at each point. It is then used in Equations 5-8 to limit local updates and to calculate the total orientation bias. For a vessel point, there are two normal directions that defined the plane in which it can induce local updates. For points on surfaces, there is a single normal direction in which updates are locally well defined. The general equation for the matrix that captures the normal direction(s) for vessel and surface points $x_i$ is $$N_i = \sum_j T(n_{ji}) \circ T(n_{ji}) \text{ for all } j \text{ normal directions } n_{ji} \text{ at } x_i \quad (11)$$

The symbol ○ denotes the outer product operator. The remaining global rigid registration equations, Equations 5-8, are unchanged and still provide the same benefits regarding induced updates and global biases.

Piecewise rigid registration: Initialized using the global rigid registration results, this step proceeds coarse-to-fine using the vascular tree hierarchy as described above. After vessel-based piecewise rigid registration, the surface is rigidly registered independently with the ultrasound image using gradient ascent and the metric in Equation 10.

Piecewise deformable registration: Initialized using the piecewise rigid registration results, the method solves for the deformable registration of the vessels to the ultrasound data and then uses their deformation field to initialize the deformable registration of the surface to the data. As detailed above, the process of piecewise deformable registration uses the natural hierarchical relationship between vessels (as tree structures) to implement a coarse-to-fine optimization scheme. First, the vascular roots are deformed to fit the data, and then their branches are deformed. This process requires 20-30 seconds. The vessel model deformations are extrapolated to the surface by evaluating the deformation field interpolation equation (Equation 9) at the surface points. The fit of the surface to the data is then refined using Equation 10 and a gradient ascent optimization strategy. As with vessels, optimization is directed by the normalized and unbiased gradients at the surface points as defined by Equation 7, and updates are dampened by an internal energy term based on the difference between each surface point's initial and current Gaussian curvature. That is, just as the present deformable vessel registration process resembles an explicit snakes technique (applied hierarchically), the present surface deformation technique is a variant of explicit active surfaces that maximizes the integral of the scaled intensities it encounters while minimizing internal energy as measured by bending.

(4) Intra-operative Desired PLL-RFA Site Transcription: From the model deformations, each desired PLL-RFA point is transcribed into the ultrasound data's coordinate system from the pre-operative data using Equation 9—the deformation field interpolation strategy of (Pennec 2003).

This integrative surface and vessel registration process, while simple, is novel, accurate, fast, and provides a consistent philosophy for handling vessels and surfaces that is absent from other intra-operative registration strategies. It is also extensible to include aspect of the physics of liver deformation and ultrasound acquisition.

C. SA2: Integrating Physics of Liver Surface and Vessel Deformation

Deformation field interpolation via Equation 9 makes numerous assumptions regarding how local liver and vessel deformations combine to specify the movement of surrounding liver tissues. One motivation for the use of deformation field interpolation is described above. Here its limitations are discussed and corrected. In particular, an often-overlooked limitation/assumption is identified and an alternative is offered.

Simple Gaussian interpolation, as in Equation 9, has limitations; the deformations must be small and smooth for the interpolated deformation vectors to be diffeomorphic and accurate. These limitations are well known. One often/completely overlooked assumption, however, is that the deformation vectors being interpolated are assumed to completely describe the deformation field at those points, and this is largely untrue.

For deformable registration strategies, the deformation vector at a model point favors the component of the deformation field normal to the model point; the tangential component of the deformation field is not included. Here Equation 9 is corrected to enable the accurate interpolation of deformation fields given sparse, limited support, i.e., given deformation field values at model points where those values selectively capture only a subspace component of the local deformation field.

To correctly estimate the deformation field vector at a desired PLL-RFA point x, the influence of the normal direction(s) $N_i$ on their $d_i$ must be considered. Therefore, each $d_i$ is weighted by the uniqueness of its basis $N_i$ compared to the total basis of all of the local deformation vectors $d_i$ that contribute to x. This total basis is a weighted sum of the normal matrices of the local model points:

$$B(x) = \sum_{i=1}^{n} N_i G_\sigma(x - x_i) \tag{12}$$

This equation parallels the global bias measure in Equation 6, but here it is making only a local bias measure. The weighting/uniqueness of each deformation vector $d_i$ is then defined as the portion of the local bias that arises from its basis as follows:

$$W_i(x) = B^{-1}(x) N_i \tag{13}$$

Applying this weighting to the model deformation vectors yields the deformation field value at x being $$D(x) = \sum_{i=1}^{n} W_i(x) d_i G_\sigma(x - x_i) \tag{14}$$

Figures 15A, 15B, 15C, 15D, 15E:
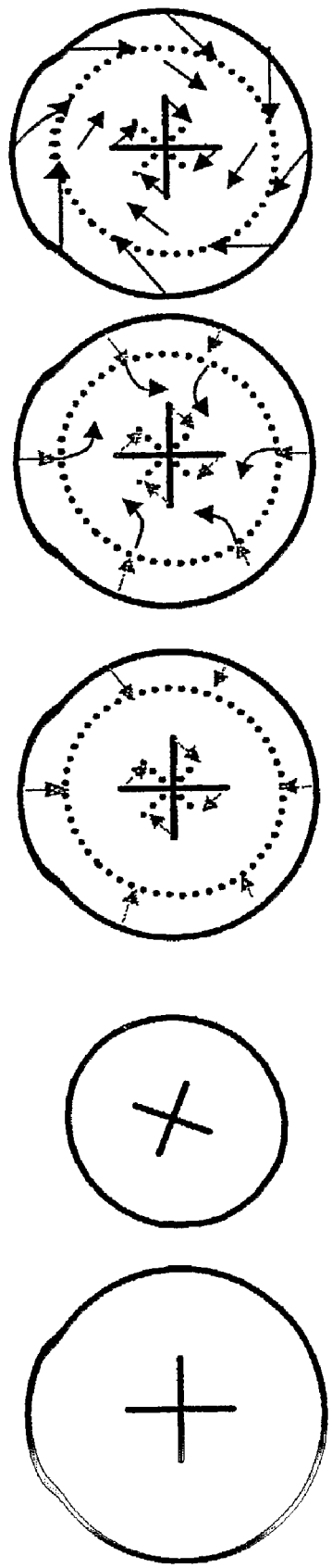
FIG. 15A is a diagram illustrating an exemplary pre-operative blood vessel model.
FIG. 15B is a diagram illustrating an exemplary intra-operative blood vessel model.
FIG. 15C is a diagram illustrating local changes to match the model from FIG. 15A to the image of FIG. 15B.
FIG. 15D is a diagram illustrating swirl induced by smooth interpolation of the deformation field produced by mapping a model in FIG. 15A to the image of FIG. 15B.
FIG. 15E is a diagram illustrating deformation field interpolation considering the limited basis of each gradient of FIG. 15D.

To visualize the importance of this approach, consider the non-rigid registration of a "pre-operative" image of a large circle with an embedded cross and an "intra-operative" image that contains a smaller circle and cross, with rotation, FIGS. 15A and 15B. The "correct" deformation from the pre- to the intra-operative image is ambiguous; many vector field transforms could be applied to map these images. However, if local feature matching is used, the vector field implied is shown in FIG. 15C.

If a smoothing-based interpolation (Equation 9) is applied to determine how the space between the circle and the cross is deformed, the likely results is shown in FIG. 15D—a swirl is introduced—this interpolation does not consider the orientation biases of the features in the image. The outer circle's local vectors tell us nothing about rotation and the inner cross' vectors poorly capture scale. The biases $N_i$ of points on the circle and points on the cross are orthogonal, so their gradient vectors should linearly combine, as in Equ. 14 and as shown in FIG. 15E. The resulting transform is nearly a similarity (rigid+scale) transform; a lower-order transform; it has a smaller Jacobean trace; it is more likely the underling process from A to B.

The above example is a simple case, but in more complex situations the present deformation field interpolation strategy remains applicable. Admittedly, there are other strategies by which similar results could be achieved for the data in FIG. 15A and FIG. 15B, e.g., by first solving for an affine transform prior to solving for the non-rigid transform. However, such strategies will not work in the more general case—when non-rigid deformations are truly present and model points only capture the portion of the local deformation field in their normal directions This is the case for nearly every model, active-contour, active-surface, or active shape deformable registration strategy. Equation 14 explicitly handles such cases; it better captures the underlying physics of the deformation field as specified by vessel and surface models. The next section describes the physics of ultrasound acquisition and extensions of the subject matter described herein that account for such physics.

D. Integrating the Physics of Ultrasound Acquisition

Figure 16:
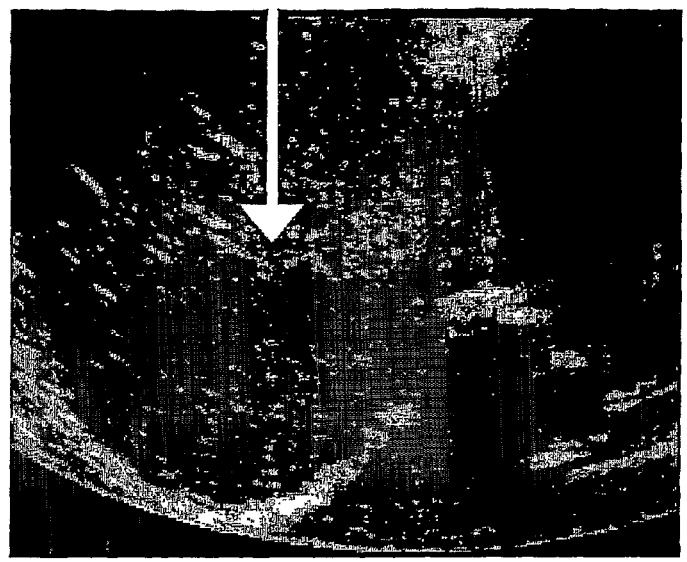
FIG. 16 is an image illustrating portions of a liver surface where arrows indicate strong gradients.

There are two aspects of the physics of ultrasound acquisition that should be considered when combining surface and vessel measures for registration: (1) Organ surfaces are visible in ultrasound images as intensity surfaces or gradient surfaces dependent upon the change in the acoustic properties across the organ surface and the orientation of the organ surfaces with respect to the ultrasound wave (FIG. 16). In FIG. 16, the arrows indicate the portions of the liver surface that are represented via strong gradiance or bright intensities in the image. The image properties of surfaces and ultrasound vary by their orientation with respect to the ultrasound wave. The present enhanced metric accounts for this dependency. (2) The influence of vessel and surface measures must be scaled to have equal influence on the metric.

(1) The present metric is modified to account for the interdependence between ultrasound wave direction and the surface normal orientation. The modification includes pre-computing the orientation of the ultrasound wave at every voxel in the 3D ultrasound data as $u(x_i)$. The dot product between the wave orientation and the vessel point's transformed normal direction $T(n_{1i})$ is computed to weight the local gradient and intensity image information at surface points. The weighting $w^I_i$ of the ultrasound image surface intensity measure $s^I_i$ at $T(x_i)$ is defined so that when the surface normal and ultrasound wave orientation are aligned, the ultrasound intensity information is favored, $$w^I_i = T(n_{1i}) \cdot u(T(x_i)) \tag{15}$$

$$s^I_i = I_\sigma(T(x_i)) \tag{16}$$

Similarly, the weighting $w^{\nabla I}_i$ of the ultrasound image gradient measure at $T(x_i)$ is defined so that when the transformed surface normal and ultrasound wave orientation are orthogonal, the image gradient information in the normal direction $s^{\nabla I}_i$ is favored, $$w^{\nabla I}_i = 1 - T(n_{1i}) \cdot u(T(x_i)) \tag{17}$$

$$s^{\nabla I}_i = \nabla I_\sigma(T(x_i)) \cdot T(n_{1i}) \tag{18}$$

(2) It is necessary to balance the influence of the vessel intensity, surface intensity, and surface gradient measures so that their responses equally influence the registration process, i.e., the metric. The normalization of these disparate measures is determined using statistics from the 15 scans reserved for system development. First, however, inter-scan intensity variations are accounted for so that the normalization statistics are constant across ultrasound scans.

The method of dynamic intensity remapping of (Pennec 2003) is used to solve for the degree-two polynomial that rescales the vessel, surface, and liver intensities in an ultrasound image to match the expected values of those intensities as defined by a template ultrasound image. As did Pennec, as the transform is optimized, the ultrasound intensities are sampled where the transformed models suggest that vessel, surface, and liver intensities are present. Using the measured means of those class' intensities, the present method solves for the degree-two polynomial that brings them into closer correspondence with template means for those classes. A prior is used to constrain the parameters of the polynomial, and only small parameter changes are allowed at each step, as registration progresses. Template means are chosen by hand labeling vessel, surface, and liver points within a training ultrasound image. Pennec has shown this method to be effective not only for simple intra-modality (ultrasound-ultrasound) matching, but also for more complex MR to CT intensity matching. Once the intensities are matched across scans, the statistics needed to equate vessel intensities, surface intensities, and surface gradients can be computed so as to give those measures commensurate units as described next.

To give commensurate units to the intensity and gradient measures in the metric, the measures are converted to likelihood measures. Specifically, using the 15 scans reserved for system development, after matching their intensities using the method described above, the present method will measure the means and variances of the vessel (Equation 3) and surface (Equations 16 and 18) measures at model points after model-image registration and for random offsets and rotations from registration. Each value v of measure m is then scaled based on its signed distance from each mean, normalized by their variances, and then normalized by the spread of the means as follows $$Z(v) = \frac{\left(\frac{v - \mu_{m,registered}}{\sigma_{m,registered}} + \frac{v - \mu_{m,unregistered}}{\sigma_{m,unregistered}}\right)}{\left(\frac{\mu_{m,registered} - \mu_{m,registered}}{\sigma_{m,registered}}\right)} \quad (19)$$

This equation is optimal linear classifier for measure v assuming equal priors, normal distributions, and $\mu_{registered} > \mu_{unregistered}$. It has a value of 1 when v is equal to $\mu_{registered}$; a value of 0 when v is equally likely to indicate registration or mis-registration; and is equal to −1 at $\mu_{unregistered}$ (if $\sigma_{registered}$ equals $\sigma_{unregistered}$).

Using this likelihood-based normalization of surface and vessel measures, the metric is defined by $$F(R, o) = \frac{1}{\sum_{i=1}^{n_{Vessel}} w_i} \sum_{i=1}^{n_{Vessel}} w_i Z(I_{\kappa r_i}^{inv}(T(x_i))) + \frac{1}{n_{Surface}} \sum_{i=1}^{n_{Surface}} [w_i^I Z(s^I(T(x_i))) + w_i^{\nabla I} Z(s^{\nabla I}(T(x_i)))] \quad (20)$$

While this equation is still an imprecise representation of the appearance of vessels and surfaces in ultrasound data, it captures more of the physics of ultrasound acquisition than any other technique (King 2001a,b; Pennec 2003). This metric considers surfaces and vessels, adjusts for ultrasound probe orientation, adjusts for inter-scan intensity variations, and normalizes the surface and vessel measures to have equal influence on the metric. The preliminary results show that the vessel component of this metric is fast and accurate for MR/CT to ultrasound registration. Next the computational costs and benefits of these extensions are determined.

E. Evaluation of Implementations Using PLL-RFA Data

This section seeks to quantify how the proposed extensions aid in the speed and accuracy of CT/MR to ultrasound intraoperative registrations for PLL-RFA. The extensions will be compared using recorded, clinical PLL-RFA data.

The accuracy of the image registration component of an ultrasound annotation system is quantified by how closely it can transcribe a point designated on pre-operative CT/MR data into its correct position in the intra-operative ultrasound data. The speed of the image registration component is measured by the time required to register an intra-operative 3D ultrasound image with a pre-operative CT/MR image.

To establish truth for the accuracy measures, an interventional radiologists will designate the desired PLL-RFA sites on each of the 4 intra-operative 3D ultrasound images from the 45 patients designated for system testing. These are patients undergoing PLL-RFA treatment, so their tumors are visible on those scans as a clinical requirement. The interventional radiologists will have already (Aim 1) designated the desired PLL-RFA site on the pre-operative data for each tumor of interest.

The four independent variables to be studied are
  Type of features used for registration (3 values): Vessel-only, Surface-only, Vessel-Surface
  Use of deformation physics, i.e., enhanced deformation field interpolation (2 values): Yes/No
  Use of ultrasound physics, i.e., probe orientation with normalized measures (2 values): Yes/No
  Ultrasound image type (2 values): B-Mode or Doppler For accuracy, the present focus is not central tendencies or variance of accuracy, but instead the key statistics for clinical accuracy are the extremes; therefore, the present method focuses on the $95^{th}$, $99^{th}$, $100^{th}$ (maximum) quantities of error. One-way ANOVA (analysis of variance) tests will be conducted to compare the 24 possible combinations of the independent variables, where the dependent variables for comparison are the 95, 99, and $100^{th}$ quantile of the log-transformed distances between the transcribed desired PLL-RFA sites and their manually designated locations within the ultrasound data. The log-transformation is used to ensure the validity of normal assumption (Muller and Fetterman 2002, page 219). The Tukey test will be used to compare the difference among all the different levels for the independent variables. Since three hypotheses are to be compared (one for each quantile), alpha=0.05/3 will be used as the significance level to adjust Type I error (Kirk 1995).

For speed, again the present focus is not central tendencies and variance of time, but instead the key clinical statistics are the $95^{th}$, $99^{th}$, $100^{th}$ (maximum) quantile of the time to register the data. The above one-way ANOVA tests are repeated to compare the 24 possible combinations of the independent variables, where the dependent variables are the 95, 99, and $100^{th}$ quantile of registration time. Again, the Tukey test will be used to compare the different levels for the independent variables, and 0.05/3 will be used for alpha.

For speed and accuracy, repeated measure ANOVA will also be used to analyze the data. Repeated measures ANOVA, where the patient is the repeated measure unit, accounts for the correlations of the measures resulting from using multiple scans from the same patient. The outcomes in the analysis will be the log-transformed discrepancy distance and registration times based on readings from the tumors in all patients. By performing the complete set of tests (every possible combination of the independent variables), the factor of each independent variable as well as their interaction can be analyzed. It will be possible to quantify how important physically based interpolation is to a vessel-only model as well as determine which is the most accurate and fastest method.

Figure 17:
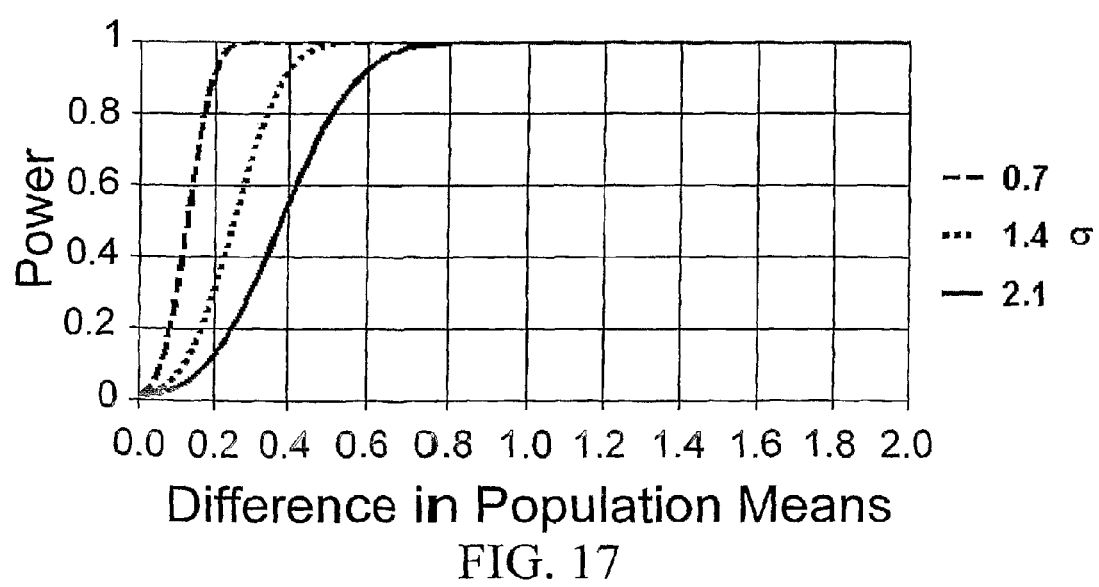
FIG. 17 illustrates power graphs used to evaluate the accuracy of the registration methods described herein.

Power analyses have been conducted. Assuming that each of the 45 patients has only one qualifying tumor (size less than 5 cm) that is captured in 4 images, then n=180. Using an alpha of 0.05/3=0.1666 since three hypotheses are being tested, then the power chart in FIG. 17 is applicable to the present pair-data hypothesis experiments. More particularly, FIG. 17 illustrates power graphs that assume that each of the 45 patients has only one qualifying tumor that appears in four images and that use an alpha of 0.05/3=0.166. Since three hypotheses are being tested, it is expected that 0.2 mm differences at the 95, 99, or $100^{th}$ quantile of accuracy or speed with a 0.9 power will be detectable. Based on Monte Carlo results (Table 2), the standard deviation of a registration method's accuracy is estimated to be ~0.7 mm. Therefore, if the expected difference between any two systems at any quantile is greater than 0.2 mm, the present method will be able to detect it with a power of 0.9. If the standard deviation were to double to 1.4 mm, the present tests would be able to detect 0.4 mm differences with a power of 0.9.

Regarding clinical accuracy requirements, each implementation's maximum error will be compared with the clinical goals of 5 mm maximum error as stated by others (King 2001a,b) and radiologists, primarily based on the desire for a 1 cm burn margin around each tumor. For each implementation, the alternative hypothesis that on average it provides less than 5 mm error at its $100^{th}$ quantile of accuracy will be tested. Given n=180, alpha=0.05, σ=0.7 mm (Table 2), and given that the initial experiments described above had a maximum error of 2.2 mm, the power to detect a difference is 1.0. More simply, each system will be judged as unacceptable if any of its registrations produced a maximum error of more than 5 mm.

Clinical image registration speed requirements are not easily measured. There are many factors that influence acceptable speed. Delays between image acquisitions in CT-guided PLL-RFA are often acceptable if a patient's only other option is open surgery. However, it has been shown that waiting several minutes between requesting an intra-operative scan and viewing the results reduces the accuracy with which a physician can guide a needle to a point and increases the length of a procedure (Sheafor 1998). After much discussion with radiologists, 30 seconds has been selected as the cut-off time between a truly "effective" intra-operative registration strategy and one whose lack of speed may ultimately degrade a physician's ability to accurately place a needle. Any system will be determined to be clinically unacceptable if any of its 180 test registrations requires more than 30 seconds to complete. While this may seem like a weak test, of the many systems reviewed in this proposal, e.g., (King 2001a,b; Porter 2001; Roche 2001; Pennec 2003), only the proposed method is likely to pass it. The present preliminary implementation performs deformable registrations in 20-30 seconds. The other systems reviewed require 5-10 minutes per registration, which is 10 to 20 times of a radiologist's suggested limit.

The subject matter described herein addresses the key component of image-based ultrasound annotation, intra-operative deformable registration of pre-operative CT/MR images with intra-operative 3D ultrasound images. It promotes the use of vascular and surface models from the pre-operative images to drive the registration process. One of its strengths is that those models specify the location, scale, orientation, and type of measure to be made in the intra-operative data to determine the validity of a transform. Those focused measures also specify how the parameters of the deformable transform should be updated to improve the registration of the pre- and intra-operative data. This makes the system uniquely accurate and fast. Extensions based on the physics of ultrasound acquisition and liver vessel and surface deformation are described herein. These extensions embody a philosophy that is applicable to other deformable registration strategies. Extensive and well-powered tests to compare the accuracy and speed of the base and extended implementations using clinical PLL-RFA data are also described. An ultrasound annotation system that meets radiologists' speed and accuracy requirements does not exist; preliminary results indicate the present implementation will be the first.

Although the examples described herein for hierarchical model-to-image registration relate primarily to surgical guidance applications, the subject matter described herein is not limited to such applications. For example, the registration methods described herein may be used in any application in which it is desirable to rapidly register a blood vessel model with blood vessel image data. Examples of such applications include disease diagnosis, disease staging, surgical planning, transplant planning, etc.

V. Reference List

The following citations correspond to the shortened citations listed above. Each of the references represented by these citations is hereby incorporated herein by reference in its entirety.

(Aylward 1996) S. Aylward, E. Bullitt, S. M. Pizer, D. Eberly, "Intensity ridge and widths for tubular object segmentation and registration." IEEE Workshop on Mathematical Methods in Biomedical Image Analysis, 131-138.

(Aylward 2001) Aylward S, Weeks S, and Bullitt E, "Analysis of the Parameter Space of a Metric for Registering 3D Vascular Images" MICCAI 2001, pages 8.

(Aylward 2002a) Aylward S, Bullitt E, "A Comparison of Methods for Tubular-Object Centerline Extraction," IEEE Transactions on Medical Imaging, 21(2), 2002 pp. 61-76.

(Aylward 2002b) Aylward S, Jomier J, Guyon J P, Weeks S, "Intra-Operative 3D Ultrasound Augmentation." IEEE International Symposium on Biomedical Imaging, July, 2002, pages 4.

(Aylward 2003) Aylward S, Jomier J, Weeks S, Bullitt E, "Registration of Vascular Images," International Journal of Computer Vision, To Appear 2003, pages 15.

(Ballard 1981) Ballard D H, "Generalizing the Hough transform to detect arbitrary shapes," Pattern Recognition, vol. 13, no. 2, pp. 111-122, 1981.

(Besl 1992) Besl P J and McKay N D "A method for registration of 3-D shapes" IEEE Trans. Pattern Anal. Mach. Intell. 14, 1992, pp. 239-56.

(Blackall 2001) J. M. Blackall, A. P. King, G. P. Penney, A. Adam, D. J. Hawkes, "A Statistical Model of Respiratory Motion and Deformation of the Liver." MICCAI 2001 1338-1340.

(Blackall 2002) J M Blackall, "Respiratory Motion in Image-Guided interventions of the Liver." PhD Dissertation, Guy's, King's, and St. Thomas' School of Medicine, King's College London 2002.

(Bookstein 1994) F. L. Bookstein and W. D. K. Green. The biometrics of landmarks and edgels: A new geometry of prior knowledge for medical image understanding. In Proc. AAAI Symposium on Applications of Computer Vision in Medical Image Processing, pages 134-137, March 1994.

(Box 1978) G. E. P. Box, W. G. Hunter, J. S. Hunter, "Statistics for Experiments." Wiley Series in Probability and Mathematical Statistics. John Wiley and Sons, New York, N.Y.

(Bucholz 1997) Bucholz R D, Yeh D D, Trobaugh J, McDurmont L L, Sturm C, Baumann C, Henderson J M, Levy A, Kressman P. The correction of stereotactic inaccuracy caused by brain shift using an intraoperative ultrasound device. In: Troccaz J, Grimson E, Moesges R (eds): CVRMed-MRCAS '97, pp 459-466.

(Bullitt 1997) E. Bullitt, A. Liu, S. Aylward, and S. Pizer. Reconstruction of the intracerebral vasculature from MRA and a pair of projection views. In Information Processing in Medical Imaging, pages 537-542, Poultney, Vt., 1997.

(Bullitt 1999) E. Bullitt, A. Liu, S. Aylward, C. Coffey, J. Stone, S. Mukherji, and S. Pizer. Registration of 3d cerebral vessels with 2d digital angiograms: Clinical evaluation. Academic Radiology, 6:539-546, 1999.

(Bullitt 2001a) Bullitt E, Aylward S, Bernard E, Gerig G, Special Article. "Computer-assisted visualization of arteriovenous malformations on the home pc." Neurosurgery: 48: 2001, pp. 576-583.

(Bullitt 2001b) Elizabeth Bullitt, Stephen Aylward, Keith Smith, Suresh Mukherji, Michael Jiroutek and Keith Muller, "Symbolic description of intracerebral vessels segmented from magnetic resonance angiograms and evaluation by comparison with X-ray angiograms" Medical Image Analysis 5:157-169, 2001.

(Collignon 1995) Collignon A, Maes F, Delaere D, Vandermeulen D, Suetens P and Marchal G, "Automated multi-modality image registration based on information theory" Information Processing in Medical Imaging 1995 ed Y Bizais, C Barillot and R Di Paola (Dordrecht: Kluwer Academic, 1995 pp 263-74.

(Chui 2001) Haili Chui, Lawrence Win, Robert Schultz, James S. Duncan, Anand Rangarajan, "A Unified Feature Registration Method for Brain Mapping." Information Processing in Medical Imaging 2001: 300-314.

(Dryden 1998) Dryden I and Mardia K 1998 Statistical Shape Analysis (New York: Wiley).

(Fenster 1996) A Fenster, D B Downey, "3D Ultrasound Imaging: A Review" IEEE Engineering in Medicine and Biology, 15:41-51 1996.

(Ferrucci 1990) J. Ferrucci, "Liver-tumor imaging—current concepts," American Journal of Roentgenology, Vol 155(3) 473-484.

(Ge 1996) Y Ge, CR Maurer Jr, J M Fitzpatrick. Surface-based 3-D image registration using the Iterative Closest Point algorithm with a closest point transform. Medical Imaging 1996: Image Processing, Proc. SPIE, 1996.

(Gobbi 2001) D Gobbi, B Lee, T Peters (John P. Robarts Research Institute, Canada), "Real-time 3D ultrasound for intraoperative surgical guidance", SPIE Medical Imaging, February 2001.

(Herline 1999) A J Herline, J D Stefansic J P Debelak, S L Hartmann, C W Pinson, R L Galloway, W C Chapman, "Image-Guided Surgery: Preliminary Feasibility Studies of Frameless Stereotactic Liver Surgery" Archives of Surgery 134:644-650 1999.

(Herline 2000) A J Herline J L Herring J D Stefansic, W C Chapman, R L Galloway Jr, B M Dawant, "Surface Registration for Use in Interactive, Image-Guided Liver Surgery." Computer Aided Surgery 5:11-17 2000.

(Hill 2001) D Hill, P Batchelor, M Holden, D Hawkes, "Medical Image Registration" Phys. Med. Biol. 46, 2001.

(Ionescu 1997) G. Ionescu, S. Lavallee, and J. Demongeot. Automated Registration of Ultrasound with CT Images: Application to Computer Assisted Prostate Radiotherapy and Orthopedics. In Second International Conference on Medical Image Computing And Computer-Assisted Intervention (MICCAI'99), volume 1679 of Lecture Notes in Computer Science, pages 768-777, Cambridge, UK, September 1999. Springer Verlag.

(Jain 1997) R K Jain "The next frontier of molecular medicine: Delivery of therapeutics," Nature Medicine 4:655-657, 1997.

(Joshi 2000) S C Joshi, M I Millier, "Landmark Matching via Large Deformation Diffeomorphisrns." IEEE TMI 9(8) 1357-1370.

(King 2000) A. P. King, J. M. Blackall, G. P. Penney, P. J. Edwards, D. L. G. Hill, D. J. Hawkes, "Bayesian Esitmation of Intra-operative Deformation for Image-Guided Surgery Using 2-D Ultrasound" MICCAI 2000 588-597.

(King 2001a) A. P. King, J. M. Blackall, G. P. Penney, D. J. Hawkes, "Tracking Liver Motion Using 2D Ultrasound and a Surface Based Statistical Shape Model" MMBIA, pages 8, 2001.

(King 2001b) A. P. King, P. G. Batchelor, G. P. Penney, J. M. Blackall, D. L. G. Hill, D. J. Hawkes "Estimating Sparse Deformation Fields Using Multiscale Bayesian Priors and 3-D Ultrasound" IPMI 2001, 155-161, 2001.

(Kirk 1995) R. E. Kirk, Experimental Design Procedures for Behavioral Science, Brooks/Cole Publishing Co., Pacific Grove, Calif. 1995.

(Lindeberg 1994) Tony Lindeberg, Scale-Space Theory in Computer Vision, Kluwer Academic Publishers, Dordrecht, Netherlands, 1994.

(McGahan 2001) McGahan JP and Dodd GD. "Perspective: Radiofrequency Ablation of the Liver: Current Status." American Journal of Roentgenology 176(1): 3-16, Jan. 2001.

(McInerney 1999) T. McInerney and D. Terzopoulos. Topology adaptive deformable surfaces for medical image volume segmentation. IEEE Transactions on Medical Imaging, 18(10):840-850, October 1999.

(Muller 1984) Muller K. E., Barton C. N. and Benignus, V. A. Recommendations for appropriate statistical practice in toxicologic experiments, Neurotoxicology, 5, 113-126, 1984.

(Pennec 2003) X. Pennec, P. Cachier, and N. Ayache. Tracking brain deformations in time-sequences of 3D US images. Pattern Recognition Letters, 24(4-5):801-813, February 2003.

(Penney 2001) G. P. Penney, J. M. Blackall, D. Hayashi, T. Sabharwal, A. Adam, D. J. Hawkes, "Overview of an Ultrasound to CT or MR Registration System for use in Thermal Ablation of Liver Metastases." Medical Image Understanding and Analysis 65-68, 2001.

(Pizer 1998) S. M. Pizer, D. Eberly, B. S. Morse, and D. S. Fritsch. "Zoom-invariant vision of figural shape: The mathematics of cores." In Computer Vision and Image Understanding, 69, 1998 55-71.

(Porter 2001) B. C. Porter, D. J. Rubens, J. G. Strang, J. Smith, S. Totterman, K. J. Parker, "3D Registration and Fusion of Ultrasound and MRI Using Major Vessels as Fiducial Markers" I EEE TMI 20(4) 2001.

(Rafaelsen 1995) Rafaelsen SR, Kronborg O, Larsen C, Fenger C, "Intra-operative ultrasonography in detection of hepatic metastases from colorectal cancer," Dis Colon Rectum. 38:355-360 1995.

(Roche 2000) A Roche, X Pennec, G. Malandain, N. Ayache, S. Ourselin, "Generalized Correlation Ratio for Rigid Registration of 3D Ultrasound with MR Images" Rapport de recherche de l'INRIA-Sophia Antipolis, #3980, Page 24

(Roche 2001) A. Roche, X. Pennec, G. Malandain, N. Ayache, "Rigid Registration of 3D Ultrasound with MR Images: a New Approach Combining Intensity and Gradient." IEEE Transactions on Medical Imaging, 20(10): 1038-1049 October 2001.

(Rohling 1998) R N Rohling, A H Gee, L Berrnian "Automatic registration of 3D ultrasound images. "Ultrasound in Medicine and Biology 24(6) 841-854.

(Rohlfing 2001) T Rohifing, C R Maurer Jr, W G O'Dell, M C Schell, J Zhong (U of Rochester), "Modeling liver motion and deformation during the respiratory cycle using intensity-based free-form registration of gated MR images", SPIE Medical Imaging, February 2001.

(Schnabel 2001) Julia A. Schnabel, Daniel Rueckert, Marcel Quist, Jane M. Blackall, Andy D. Castellano-Smith, Thomas Hartkens, Graeme P. Penney, Walter A. Hall, Haiying Liu, Charles L. Truwit, Frans A. Gerritsen, Derek L. G. Hill, David J. Hawkes: A Generic Framework for Non-rigid Registration Based on Non-uniform Multi-level Free-Form Deformations. MICCAI 2001: 573-581.

(Schorr 2000) Schorr 0, hata N, Bzostek A, Kumar R, Burghart C, Taylor R, Kikinis R "Distributed modular computer-integrated surgical robotic systems" Medical Image Computing and Computer-Assisted Intervention 2000, Pittsburgh, Pa., Lecture Notes in Computer Science, MICCAI 2000, Springer-Verlag, Vol 1935, pp. 969-987.

(Sheafor 1998) D. H. Sheafor, E. K. Paulson, C. M. Simmons, D. M. DeLong, R. C. Nelson, "Abdominal Percutaneous lnterventional Procedures: Comparison of CT and US Guidance," Radiology, 207, 705-710.

(Sobol 1994) Llya M. Sobol'. A Primer for the Monte Carlo Method. CRC Press, Boca Raton, 1994.

(Solbiati 1997) L Solbiati et al, "Percutanecous US-Guided Radio-Frequency Tissue Ablation of Liver Metastases: Treatment and Follow-Up in 16 Patients," Radiology, 202, 195-203.

(Soler 2000) L. Soler, H Delingette, G. Malandain, N. Ayache, C. Koehl, J. M. Clement, O. Dourthe, and J. Marescaux. An automatic virtual patient reconstruction from CT-scans for hepatic surgical planning. In J. D. Weswood, editor, Medicine Meets Virtual Reality, pages 316-322. IOS Press, 2000.

(Strintzes 1997) MG Strintzis, I Kokkinidis "Maximum Likelihood Motion Estimation in Ultrasound Image Sequences" IEEE Signal Processing Letters 4(6).

(van den Elsen 1994) van den Elsen P A, Maint "Registering images using correlation of geometrical features" IEEE Trans. Med. Imaging 14 1994, pp. 384-96.

(Viola 1997) P Viola, WM Wells "Alignment by Maximization of Mutual Information" International Journal of Computer Vision 24(2) 137-154.

(Wilson 1998) Wilson DL, Carrillo A, Zheng L, Genc A, Duerk J L, Lewin J S, "Evaluation of 3D image registration as applied to MR-guided thermal treatment of liver cancer" J Magn Reson Imaging 8:77-34 1998.

(Weeks 2001) S. Weeks, K. Wilber, and S. R. Aylward, "Volume estimations using conventional hand tracing techniques vs. automatic thresholding techniques: Can we be more accurate and save time?," Rad iological Society of North America}, November 2001.

(Wood 2000) T F Wood DM Rose, M Chung, D P Allegra, L J Foshag, A J Bilchik "Radiofrequency ablation of 231 unresectable hepatic tumors: indications, limitations, and complications." Annals of Surgical Oncology 7(8) 593-600.

(Wu 2001) C. C. Wu, D. C. Yeh, M. C. Lin, T. J. Liu, F. K. Peng "Improving operative safety for cirrhotic liver resection" British Journal of Surgery 88, 210-215.

(Xu 1993) L. Xu and E. Oja, "Randomized Hough Transform (RHT): Basic mechanisms, algorithms, and computational complexities," CVGIP: Image Understanding, vol. 57, no. 2, pp. 131-154, March 1993.

It will be understood that various details of the invention may be changed without departing from the scope of the invention. Furthermore, the foregoing description is for the purpose of illustration only, and not for the purpose of limitation.

What is claimed is:

1. A method for hierarchical registration of a blood vessel model to blood vessel image data, the method comprising:
    (a) mapping a vascular model for a subject to a target vascular image for the subject using a global rigid transformation;
    (b) hierarchically mapping individual vessel branches in the model using piecewise rigid transformations to form a piecewise-rigid-transformed vascular model; and
    (c) hierarchically mapping individual vessel branches in the piecewise-rigid-transformed vascular model to the target image using piecewise deformable transformations to form a piecewise-deformably-transformed vascular model.

2. The method of claim 1 wherein mapping a vascular model for a subject to a target image for the subject using a global rigid transformation includes mapping a three dimensional vascular model to the target image.

3. The method of claim 1 wherein hierarchically mapping individual vessel branches in the vascular model to the target image using piecewise rigid transformations includes performing the piecewise rigid transformations beginning from a root of a vascular tree in the vascular model and proceeding to branches of the vascular tree in a hierarchical manner.

4. The method of claim 1 wherein hierarchically mapping individual vessel branches in the piecewise-rigid-transformed vascular model to the target image includes applying the deformable registration beginning at a root of a vascular tree in the piecewise-rigid-transformed vascular model and proceeding to branches of the vascular tree in a hierarchical manner.

5. The method of claim 1 comprising generating the vascular model from vascular image data for the subject.

6. The method of claim 5 wherein generating the vascular model includes generating the vascular model from magnetic resonance (MR) image data.

7. The method of claim 5 wherein generating the vascular model includes generating the vascular model from computerized tomography (CT) image data.

8. The method of claim 1 wherein the target image includes an ultrasound image and wherein the method further comprises using the piecewise-deformably-transformed vascular model to annotate the ultrasound image.

9. A method for hierarchical registration between a blood vessel and tissue surface model for a subject and a blood vessel and tissue surface image for the subject, the method comprising:
    (a) generating a blood vessel model and a tissue surface model from a source blood vessel and tissue surface image for a subject;
    (b) performing a plurality of hierarchical registrations between the blood vessel model and the tissue surface model and a target blood vessel and tissue surface image for the subject to produce transformations between locations in between locations in the models and locations in the target image; and
    (c) determining, based on the transformations in locations, a location of a feature from the source blood vessel and tissue surface image in the transformed blood vessel and tissue surface model.

10. The method of claim 9 wherein performing a plurality of hierarchical registrations includes:

(a) performing a global rigid registration between the vascular and tissue surface models and the target image to form first transformed vascular and tissue surface models;
(b) performing a hierarchical piecewise rigid registration between blood vessels in the first transformed vascular model and the blood vessels in the target image to form a second transformed vascular model;
(c) performing a global rigid registration between the first transformed tissue surface model and a tissue surface image for the subject to form a second transformed tissue surface model;
(d) performing a hierarchical piecewise deformable registration between the second transformed vascular model and the target image to form a third transformed vascular model;
(e) performing a global deformable registration between the second transformed tissue surface model and the target image to form a third transformed tissue surface model;
(f) combining the third transformed vascular model and the third transformed tissue surface model to form a third transformed vascular and tissue surface model; and
(g) performing a deformation field interpolation to transcribe features of interest in the source image to the third transformed vascular and tissue surface model.

11. The method of claim 9 wherein performing the hierarchical registrations includes performing registrations beginning at roots of vascular trees in the vascular model and proceeding to branches of the vascular trees in a hierarchical manner.

12. The method of claim 9 wherein the source image comprises a magnetic resonance (MR) image and the target image comprises an ultrasound image.

13. The method of claim 9 wherein the source image comprises a computerized tomography (CT) image and the target image comprise an ultrasound image.

14. The method of claim 9 comprising continually repeating steps (b) and (c) to update the location of the feature.

15. A system for hierarchical blood vessel and tissue surface model to image registration, the system comprising:
(a) a blood vessel and tissue surface model generator for receiving a source blood vessel and tissue surface image for a subject and generating a vascular model and a tissue surface model for the subject; and
(b) a hierarchical blood vessel and tissue surface model-to-image registration module for receiving as input the vascular model, the tissue surface model, a target blood vessel and tissue surface image, and a feature of interest in the source blood vessel and tissue surface image and for performing hierarchical blood vessel and tissue surface model-to-image registrations to produce a model with a target-image-registered feature of interest.

16. The system of claim 15 wherein the hierarchical blood vessel and tissue surface model-to-image registration module is adapted to perform at least one registration beginning at a root of a vascular tree in the vascular model and proceeding to braches in the vascular tree in a hierarchical manner.

17. The system of claim 15 wherein the hierarchical blood vessel and tissue surface model-to-image registration module is adapted to perform at least one piecewise rigid transformation between the vascular model and the target image.

18. The system of claim 15 wherein the hierarchical blood vessel and tissue surface model-to-image registration module is adapted to perform at least one piecewise deformable transformation between the vascular model and the target image.

19. The system of claim 15 wherein the hierarchical blood vessel and tissue surface module-to-image registration module is adapted to apply a deformation field interpolation to determine a location of the target-image-registered feature of interest.

20. A computer program product comprising computer-executable instructions embodied in a non-transitory computer-readable medium for performing steps comprising:
(a) mapping a vascular model for a subject to a target vascular image for the subject using a global rigid transformation;
(b) hierarchically mapping individual vessel branches in the model using piecewise rigid transformations to form a piecewise-rigid-transformed vascular model; and
(c) hierarchically mapping individual vessel branches in the piecewise-rigid-transformed vascular model to the target image using piecewise deformable transformations to form a piecewise-deformably-transformed vascular model.

21. A computer program product comprising computer-executable instructions embodied in a non-transitory computer-readable medium for performing steps comprising:
(a) generating a blood vessel model and a tissue surface model from a source blood vessel and tissue surface image for a subject;
(b) performing a plurality of hierarchical registrations between the blood vessel model and the tissue surface model and a target blood vessel and tissue surface image for the subject to produce transformations between locations in between locations in the models and locations in the target image; and
(c) determining, based on the transformations in locations, a location of a feature from the source blood vessel and tissue surface image in the transformed blood vessel and tissue surface model.

* * * * *